(12) United States Patent
Wolf et al.

(10) Patent No.: US 11,295,860 B2
(45) Date of Patent: Apr. 5, 2022

(54) USING AT HOME MEASURES TO PREDICT CLINICAL STATE AND IMPROVING THE ACCURACY OF AT HOME MEASUREMENTS/PREDICTIONS DATA ASSOCIATED WITH CIRCADIAN RHYTHM AND MEAL TIMING

(71) Applicant: Zoe Limited, London (GB)

(72) Inventors: Jonathan Thomas Wolf, London (GB); Richard James Davies, London (GB); George Hadjigeorgiou, London (GB)

(73) Assignee: Zoe Limited, London (GB)

( * ) Notice: Subject to any disclaimer, the term of this patent is extended or adjusted under 35 U.S.C. 154(b) by 0 days.

(21) Appl. No.: 16/434,135

(22) Filed: Jun. 6, 2019

(65) Prior Publication Data

US 2019/0362848 A1    Nov. 28, 2019

Related U.S. Application Data

(63) Continuation-in-part of application No. 15/894,776, filed on Feb. 12, 2018, now Pat. No. 11,183,080, and a continuation-in-part of application No. 15/894,798, filed on Feb. 12, 2018, now Pat. No. 11,183,291, and a continuation-in-part of application No. 15/987,699, filed on May 23, 2018, and a continuation-in-part of
(Continued)

(51) Int. Cl.
*G16H 50/20* (2018.01)
*G16H 50/30* (2018.01)
*G06N 20/00* (2019.01)

(52) U.S. Cl.
CPC ............. *G16H 50/20* (2018.01); *G06N 20/00* (2019.01); *G16H 50/30* (2018.01)

(58) Field of Classification Search
CPC ....................................................... G16H 50/20
USPC ........................................................... 434/127
See application file for complete search history.

(56) References Cited

U.S. PATENT DOCUMENTS

| 7,999,674 B2 | 8/2011 | Kamen |
| 8,690,578 B1 | 4/2014 | Nusbaum et al. |

(Continued)

FOREIGN PATENT DOCUMENTS

| WO | WO0205702 | 1/2002 |
| WO | WO2008154759 A1 | 12/2008 |

(Continued)

OTHER PUBLICATIONS

The PCT Search Report dated May 21, 2019, for PCT Application No. PCT/IB2019/051088, 11 pages.
(Continued)

*Primary Examiner* — Kesha Frisby
(74) *Attorney, Agent, or Firm* — Lee & Hayes, P.C.

(57) ABSTRACT

Techniques are disclosed herein for using standardized meals and digital devices can be utilized outside a clinical setting to assist in determining/predicting one or more clinical states associated with one or more individuals. Using the technologies described herein, different techniques can be utilized to for using nutritional response measurements. For example, response measurements can be obtained for two fat meals instead of a single fat meal. Data associated with a circadian rhythm (e.g., sleep times, awake times) can also be utilized to improve the accuracy of the measured biomarkers. In other examples, biome data and other data can be utilized.

20 Claims, 18 Drawing Sheets

Related U.S. Application Data application No. 16/120,039, filed on Aug. 31, 2018, and a continuation-in-part of application No. 16/272,865, filed on Feb. 11, 2019.

(60) Provisional application No. 62/723,424, filed on Aug. 27, 2018, provisional application No. 62/733,429, filed on Aug. 27, 2018, provisional application No. 62/808,180, filed on Feb. 20, 2019, provisional application No. 62/821,949, filed on Mar. 21, 2019.

(56) References Cited

U.S. PATENT DOCUMENTS

| | | |
|---|---|---|
| 9,011,153 B2 | 4/2015 | Bennett et al. |
| 2003/0091964 A1 | 5/2003 | Yeager |
| 2009/0275002 A1 | 11/2009 | Hoggle |
| 2011/0091842 A1 | 4/2011 | Dugan |
| 2013/0216982 A1 | 8/2013 | Bennett et al. |
| 2015/0079551 A1 | 3/2015 | Egan |
| 2015/0093725 A1 | 4/2015 | Baarman et al. |
| 2015/0118659 A1 | 4/2015 | Meyer |
| 2015/0140523 A1 | 5/2015 | Dewan |
| 2015/0206450 A1 | 7/2015 | Wayman et al. |
| 2015/0294593 A1 | 10/2015 | Schoen et al. |
| 2015/0294594 A1 | 10/2015 | Pacione et al. |
| 2015/0371553 A1 | 12/2015 | Vento |
| 2016/0035248 A1 | 2/2016 | Gibbs |
| 2016/0042660 A1 | 2/2016 | Radovcic |
| 2016/0049091 A1 | 2/2016 | Omidi |
| 2016/0049092 A1 | 2/2016 | Barnett et al. |
| 2016/0063888 A1 | 3/2016 | McCallum et al. |
| 2016/0071423 A1 | 3/2016 | Sales et al. |
| 2016/0071432 A1 | 3/2016 | Kurowski et al. |
| 2016/0098942 A1 | 4/2016 | Messier |
| 2016/0140869 A1 | 5/2016 | Kuwahara et al. |
| 2016/0166195 A1 | 5/2016 | Radecka et al. |
| 2016/0232311 A1 | 8/2016 | Segal et al. |
| 2016/0253922 A1 | 9/2016 | Kremen et al. |
| 2016/0379520 A1 | 12/2016 | Borel et al. |
| 2019/0251861 A1 | 8/2019 | Wolf et al. |
| 2019/0252058 A1 | 8/2019 | Wolf et al. |
| 2019/0362648 A1 | 11/2019 | Hadjigeorgiou et al. |
| 2020/0065681 A1 | 2/2020 | Wolf et al. |
| 2020/0066181 A1 | 2/2020 | Hadjigeorgiou et al. |

FOREIGN PATENT DOCUMENTS

| | | |
|---|---|---|
| WO | WO2015166489 | 11/2015 |
| WO | WO2018031991 | 2/2018 |

OTHER PUBLICATIONS

The PCT Search Report dated May 21, 2019, for PCT Application No. PCT/IB2019/051089, 12 pages.

The PCT Search Report dated Sep. 3, 2019, for PCT Application No. PCT/EP2019/063330, 15 pages.

Final Office Action dated Jul. 10, 2020 for U.S. Appl. No. 15/894,776, "Generating Predicted Values of Biomarkers for Scoring Food", Wolf, 6 pages.

Final Office Action dated Jul. 10, 2020 for U.S. Appl. No. 15/894,798, "Generating Personalized Nutritional Recommendations Using Predicted Values of Biomarkers", Wolf, 6 pages.

Non Final Office Action dated Jan. 10, 2020 for U.S. Appl. No. 15/894,776 "Generating Predicted Values of Biomarkers for Scoring Food" Wolf, 11 pages.

Non Final Office Action dated Jan. 10, 2020 for U.S. Appl. No. 15/894,798 "Generating Personalized Nutritional Recommendations Using Predicted Values of Biomarkers" Wolf, 12 pages.

Anonymous, "Glucose meter—Wikipedia", retrieved on Oct. 30, 2019 at <<https://en.wikipedia.org/w/index.php?title=Glucosemeter&oldid=851737873#Noninvasive_meters>>, Jul. 24, 2018, 15 pages.

Carson et al, "Challenges for measurement science and measurement practice: the collection and interpretation of home-monitored blood glucose data", Measurement, vol. 24, No. 4, Institute of Measurement and Control, Dec. 1, 1998, pp. 281-293.

Edelman et al, "Multisite Evaluation of a New Diabetes Selt-Test for Glucose and Glycated Protein (Fructosamine)", Diabetis Technology & Therapeutics, vol. 2, No. 2, Jan. 1, 200, pp. 233-238.

Kulkarni, "Comparision of Image Recognition APIs on Food Images", retrieved on Oct. 19, 2019 at <<https://byles.grubhub.com/https-medium-com-rohan-kulkarni comparison-of-image-recognition-apis-on-food-images-cddc9105fc33>>, pp. 1-9.

The PCT Search Report and Written Opinion dated Nov. 22, 2019 for PCT Application No. PCT/EP2019/072806, 15 pages.

The PCT Search Report and Written Opinion dated Nov. 8, 2019 for PCT Application No. PCT/EP2019/071801, 14 pages.

The PCT Search Report and Written Opinion dated Dec. 5, 2019 for PCT Application No. PCT/EP2019/072804, 14 pages.

Seeberg et al, "Development of a weable multisensor device enabling continuous monitoring of vital signs and activity", IEEE-EMBS International Conference on Biomedical and Health Informatics (BHI), IEEE, Jun. 1, 2014, pp. 213-218.

Tushuizen et al, "Postprandial lipid and apolipoprotein responses following three consecutive meals associate with liver fat content in type 2 diabetes and the metabolic syndrome", Atherosclerosis, vol. 211, No. 1, Elsevier, Amsterdam, NL, Feb. 10, 2010, pp. 308-314.

Von Niederhausern et al, "Validity of mobile electronic data capture in clinical studies: a pilot study in pediatric population", BMC Medical Research Methodology, vol. 17, No. 1, Dec. 1, 2017, 10 pages.

Wolcott et al, "Laboratory Medicine: A National Status Report Division of Laboratory Systems National Center for Preparedness, Detection, and Control of Infectious Diseases Centers for Disease Control and Prevention—The Lewin Group under Subcontract to Battelle Memorial Institute", retrieved on Nov. 25, 2019 at <<http://www.lewin.com/content/dam/Lewin/Resources/Site_Sections/Publications/39931>>, May 1, 2008, 385 pages.

Yun et al, "Smartphone-based point-of-care lipid blood test performance evaluation compared with a clinical diagnostic laboratory method", arxiv.org, Cornell University Library, Ithaca, NY, Apr. 19, 2018, 8 pages.

Non Final Office Action dated Dec. 10, 2020 for U.S. Appl. No. 15/987,699, "Improving the Accuracy of Measuring Nutritional Responses in a Non-Clinical Setting", Hadjigeorgiou, 12 pages.

Office Action for U.S. Appl. No. 16/120,039, dated Mar. 22, 2021, Hadjigeorgiou, "Generating Personalized Food Recommendations from Different Food Sources", 12 pages.

The International Preliminary Report on Patentability dated Mar. 11, 2021 for PCT Application No. PCT/EP2019/072804, 9 pages.

| PPL TAG measure | XXL-VLDL-P | XL-VLDL-P | XXL-VLDL-C | XL-VLDL-C |
|---|---|---|---|---|
| TAG rise at 6hrs | 0.778 | 0.761 | 0.758 | 0.758 |
| TAG concentration at 6hrs | 0.766 | 0.817 | 0.785 | 0.802 |
| TAG AUC from 4 to 6 hrs | 0.658 | 0.730 | 0.691 | 0.712 |
| TAG AUC from 0 to 6 hrs | 0.615 | 0.705 | 0.659 | 0.665 |
| TAG concentration at 4hrs | 0.544 | 0.632 | 0.566 | 0.610 |
| TAG rise at 4hrs | 0.473 | 0.519 | 0.490 | 0.507 |
| TAG iAUC from 0 to 6hrs | 0.386 | 0.428 | 0.399 | 0.414 |
| TAG iAUC from 4 to 6hrs | 0.383 | 0.418 | 0.382 | 0.465 |

FIG. 6D

Predicting Glyca(GP) levels with and without postprandial information

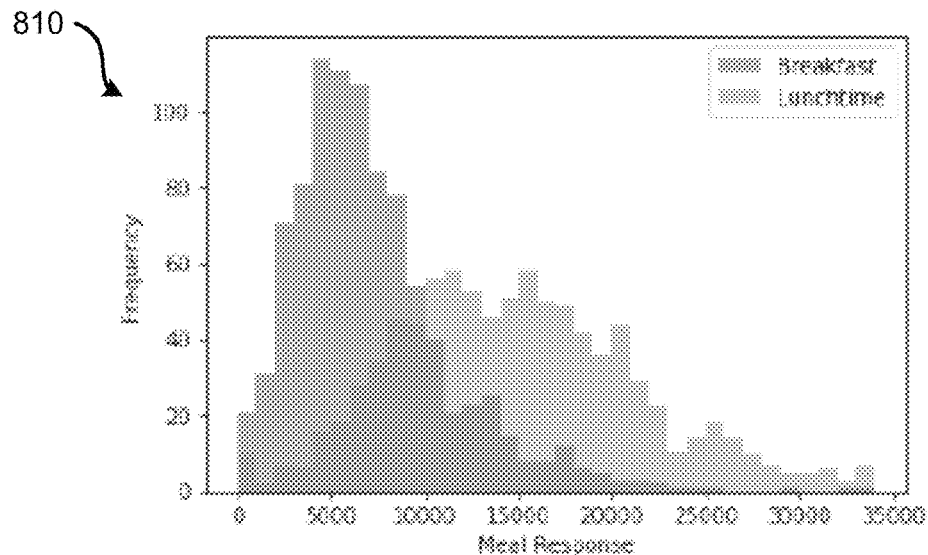
FIG. 8A
| mmol/l/sec per 2h | Median | Standard Deviation |
|---|---|---|
| Breakfast | 7,162 | 4,371 |
| Lunch | 15,228 | 6,909 |
FIG. 8B
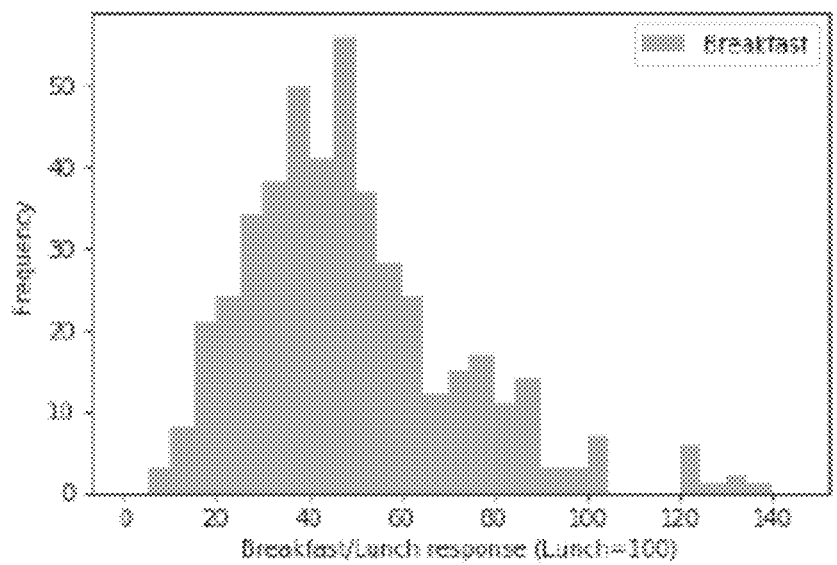
FIG. 8C

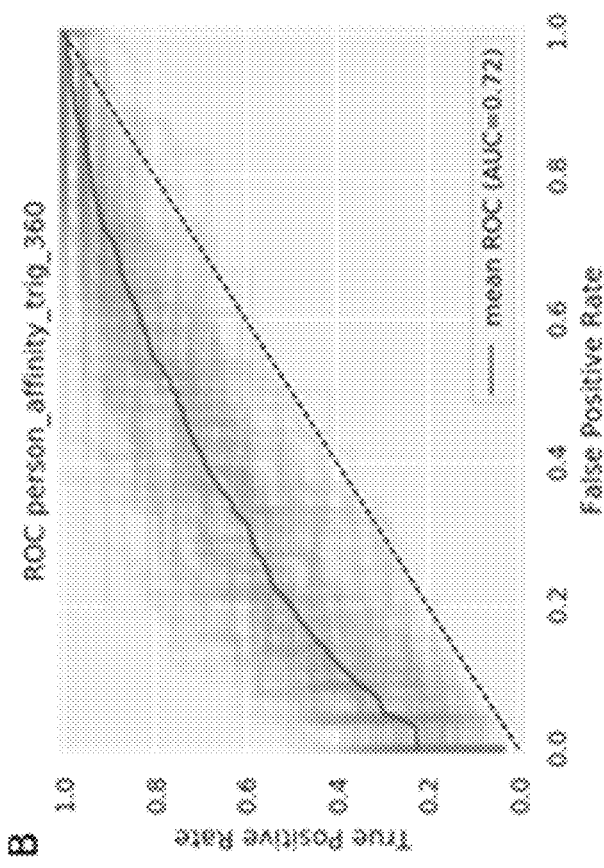
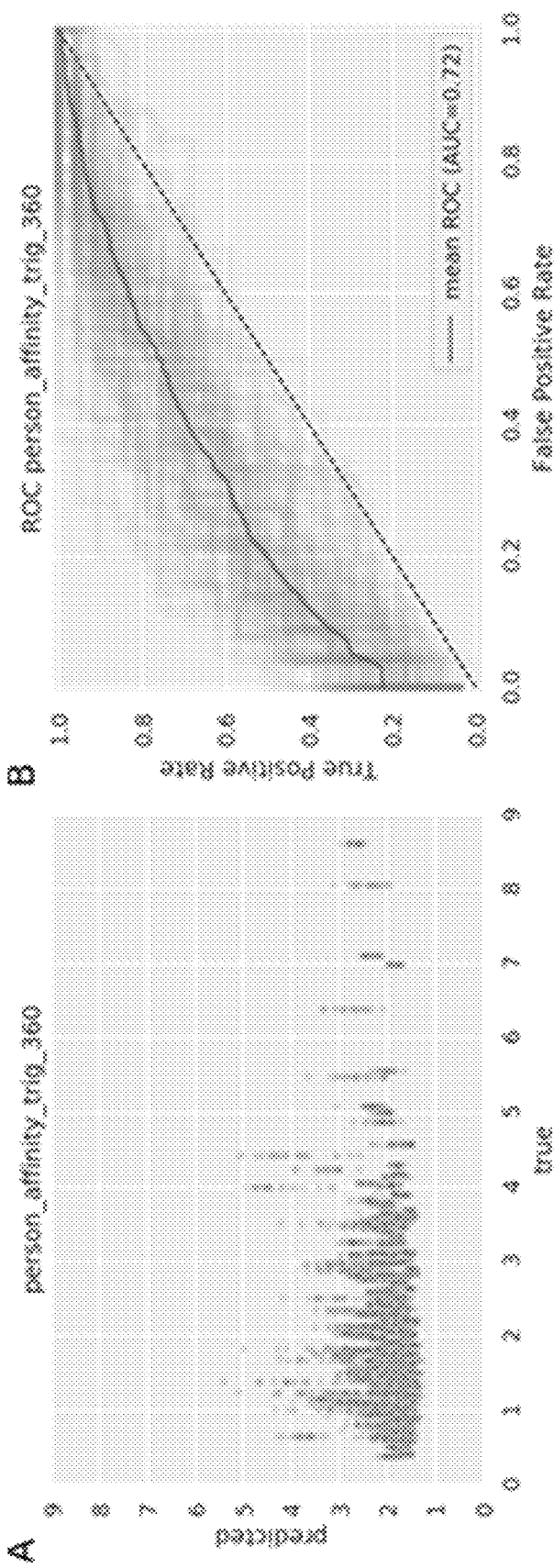
FIG. 9B
FIG. 9A

USING AT HOME MEASURES TO PREDICT CLINICAL STATE AND IMPROVING THE ACCURACY OF AT HOME MEASUREMENTS/PREDICTIONS DATA ASSOCIATED WITH CIRCADIAN RHYTHM AND MEAL TIMING

CROSS-REFERENCE TO RELATED APPLICATIONS

This application is a continuation in part of U.S. patent application Ser. No. 15/894,776, entitled "GENERATING PREDICTED VALUES OF BIOMARKERS FOR SCORING FOOD", filed on Feb. 12, 2018, U.S. patent application Ser. No. 15/894,798, entitled "GENERATING PERSONALIZED NUTRITIONAL RECOMMENDATIONS USING PREDICTED VALUES OF BIOMARKERS", filed on Feb. 12, 2018, U.S. patent application Ser. No. 15/987,699, entitled "IMPROVING THE ACCURACY OF MEASURING NUTRITIONAL RESPONSES IN A NON-CLINICAL SETTING", filed on May 23, 2018, U.S. patent application Ser. No. 16/120,039, entitled "GENERATING PERSONALIZED FOOD RECOMMENDATIONS FROM DIFFERENT FOOD SOURCES", filed on Aug. 31, 2018, U.S. patent application Ser. No. 16/272,865, entitled "IMPROVING THE ACCURACY OF TEST DATA OUTSIDE THE CLINIC", filed on Feb. 11, 2019, and also claims priority to U.S. Provisional Patent Application No. 62/723,424, entitled "GENERATING PERSONALIZED NUTRITIONAL RECOMMENDATIONS USING PREDICTED VALUES OF BIOMARKERS", filed on Aug. 27, 2018, U.S. Provisional Patent Application No. 62/723,429, entitled "GENERATING PERSONALIZED NUTRITIONAL RECOMMENDATIONS USING PREDICTED VALUES OF BIOMARKERS", filed on Aug. 27, 2018, U.S. Provisional Patent Application No. 62/808,180, entitled "USING AT HOME MEASUREMENTS TO PREDICT CLINICAL STATE AND IMPROVING THE ACCURACY OF AT HOME MEASUREMENTS/PREDICTIONS USING DATA ASSOCIATED WITH CIRCADIAN RHYTHM AND MEAL TIMING", filed on Feb. 20, 2019, and U.S. Provisional Patent Application No. 62/821,949, entitled "PREDICTOR OF GLYCEMIC RESPONSES AND PERSONAL METABOLIC RESPONSES TO FOOD PREDICTED USING MULTIOMICS MACHINE LEARNING", filed on Mar. 21, 2019, the entire contents of which are incorporated herein by reference.

BACKGROUND

Today, individuals can measure a large number of health characteristics without having to go to a lab or clinic. For instance, an individual may measure blood glucose, cholesterol, triglycerides, obtain biological samples (e.g., blood, microbiome), and the like from home or work, without having to visit a lab or clinic. These free-living measurements are often cheaper and can be easier for the individual to obtain as compared to going to a clinic. Free living measurements, however, can be less accurate than measurements taken in a clinical setting, such as in a hospital or a lab. As such, utilizing these measurements can be challenging.

BRIEF DESCRIPTION OF THE DRAWINGS

FIGS. 6A, 6B, 6C, and 6D show predicting remnant Lipoprotein levels with and without postprandial information.

FIGS. 8A, 8B, and 8C show significant variation in how individuals respond to the same meal at breakfast and lunch in at home conditions.

FIGS. 9A and 9B illustrate example results of two machine learning models: a regressor and a classifier approach in predicting the triglycerides levels at six hours.

DETAILED DESCRIPTION

The following detailed description is directed to technologies for using at home measurements to predict clinical state and improve the accuracy of the at home measurements/predictions using data associated with the timing of meals.

According to some configurations, standardized meals and digital devices can be utilized outside a clinical setting to assist in determining/predicting one or more clinical states associated with one or more individuals. A clinical state can include but is not limited to a state such as a diabetic state, a prediabetic state or one or more metabolic syndrome states, and the like. The standardized meals and digital devices can also be utilized to predict risk of a disease risk/health outcome (e.g. % risk of cardiovascular disease over the next decade). As will be appreciated, these are just a few of the examples.

According to some techniques, nutritional response measurements are obtained for two fat meals instead of a single fat meal. The second fat meal can be eaten at some period of time (e.g., a few hours) after the first fat meal. The use of two meals results in a higher variation of response compared to a single fat meal. In some instances, the second meal may not have fat in it. This second meal provides discrimination to better determine an individual's postprandial responses, such as the response of many different types of lipids to a meal. An individual's postprandial responses may not be well differentiated from average responses when obtained with a single meal eaten outside of the clinic which is an environment with lower levels of accuracy. This discrimination outside the clinic was uncertain until more than one fat meal was utilized. In some examples, using a single meal at home and blood collection methods such as dried blood spots the results between individuals cannot be significantly differentiated.

It was previously thought that one could feed a patient a large high fat meal at home and measure lipid results a few hours later and get a good measure of response. However, these post-prandial lipid tests have largely been done in clinical settings where accuracy of measurements are much higher, there are far fewer confounding factors, often the participants are suffering from diseases that lead to high lipid responses, participants may stay in the lab for as much as 8 hours, and where the focus is on average responses rather than individual responses.

Figure 1:
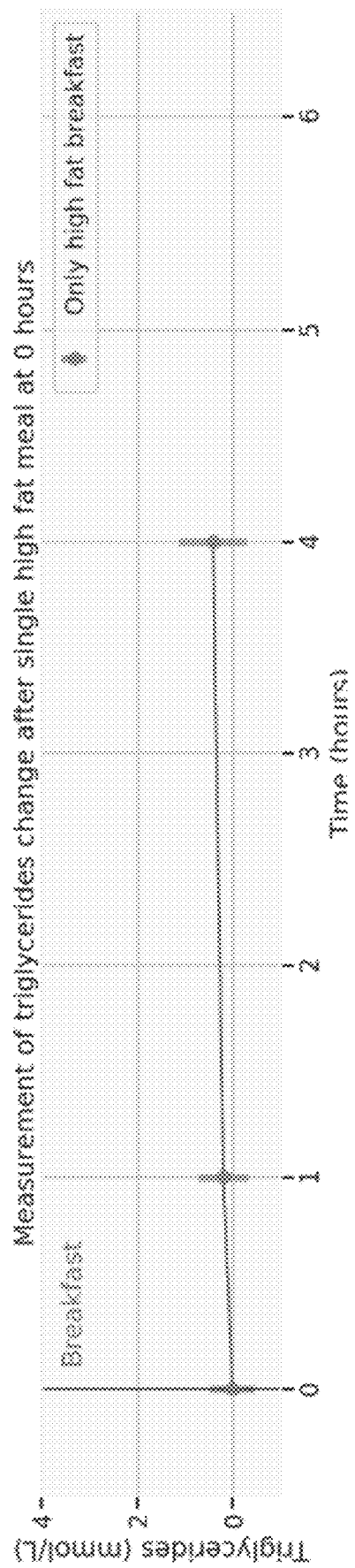
FIG. 1 shows the rise of postprandial triglycerides after a single high fat meal measured at home.

FIG. 1 shows that when a postprandial triglycerides measurement is done in non-clinical conditions with a single fat meal the human body does not respond as was anticipated, and the responses are highly clustered with a small average response. As a result, this sort of single meal protocol may be less useful than anticipated to measure postprandial responses for lipids or similar biomarkers, especially as at home measurement are likely to be less accurate than in the clinic. According to some examples, in order to obtain a high variation of response at home, the individual consumes a second meal.

As illustrated, FIG. 1 shows the rise of postprandial triglycerides, measured at 1 h and 4 h after a breakfast consisting of a standardized muffin containing 40.5 g of carbs and 34.8 of fat consumed at home. At 4 hours the average rise is 0.41 with a standard deviation of 0.70. This measurement was performed on 259 individuals of which only 213 (~82%) had a triglycerides at 4 h higher than at fasting.

Figure 2:
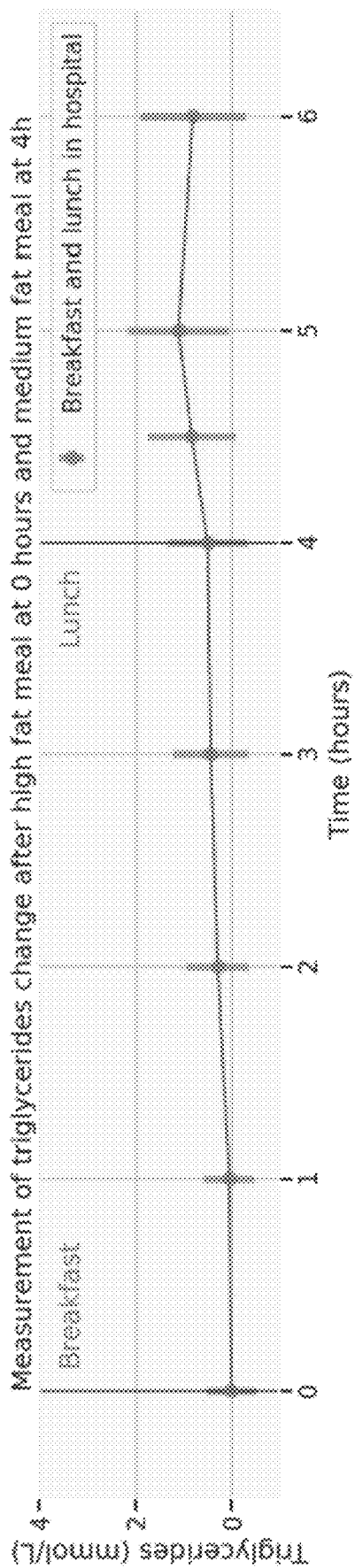
FIG. 2 shows the rise of postprandial triglycerides measured at several time points.

FIG. 2 shows a two meal protocol measured in the clinic. This demonstrates that a second meal generates a high variation of lipid response in a clinic. Clinical tests have previously shown that a second meal may help to rapidly push up lipid levels in the blood if there was previously a fat meal, possibly by pushing lipids out of the lining of the gut and into the blood. It was unknown if this would lead to a high variation in individual responses outside the clinic to an extent large enough to be measurable using at home technologies.

Figure 3:
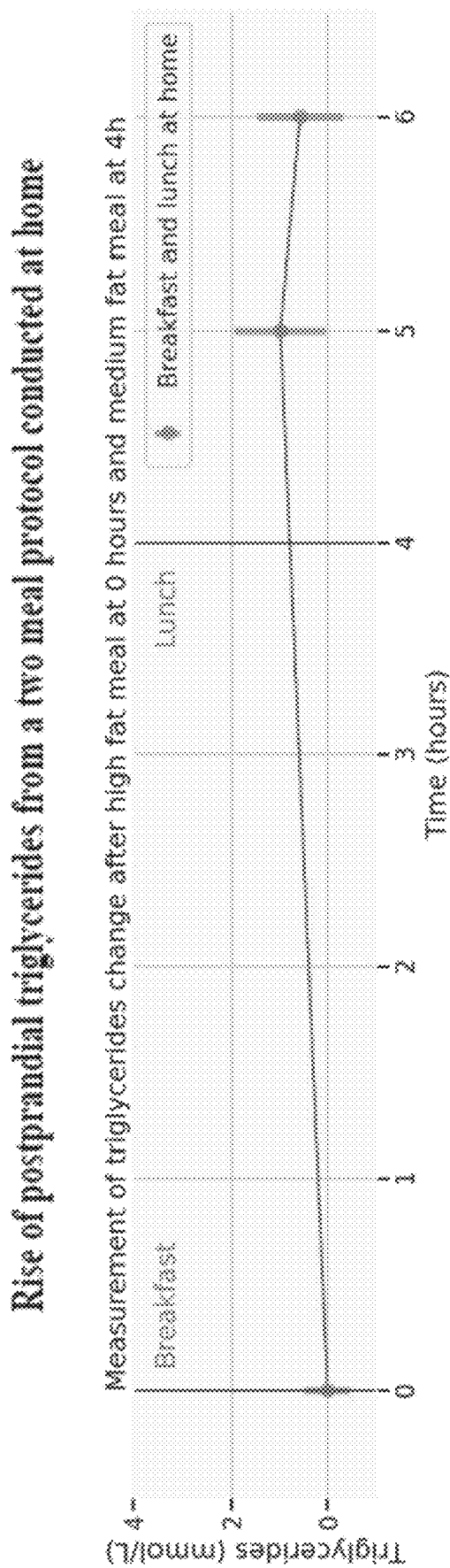
FIG. 3 shows the rise of postprandial triglycerides from a two meal protocol conducted at home

As illustrated, FIG. 2 shows the rise of postprandial triglycerides measured at several time points. Breakfast was consumed at 0 h and at 4 h lunch was consumed. At 4 h the average rise is 0.49 with a standard deviation of 0.80 while at 5 h the average rise is 1.09 with a standard deviation of 1.04. At 5 h the rise is approximately double that at 4 h and with a larger variation in the population. This measurement was performed on 598 individuals of which 549 (~91%) had a triglycerides at 5 h higher than at fasting FIG. 3 demonstrates that the use of a second meal can generate a high variation in individual lipid responses outside the clinic to an extent large enough to be measurable using at home technologies. It was also unknown if these measurements would be repeatable or chance:

As illustrated, FIG. 3 shows the rise of postprandial triglycerides measured at 5 h and 6 h after a breakfast and lunch were consumed at 0 h and 4 h respectively at home. At 5 h and 6 h the mean rise from fasting levels is 0.98 and 0.57 respectively, with standard deviations of 0.93 and 0.88. The meals consisted of breakfast with 28.2 g of carbs and 39.3 g of fat and a lunch with 71.2 g carbs and 22.2 g of fat. This protocol was carried out 615 times (often in duplicate per individual). On 597 occasions (~97%) the triglycerides at 5 h were higher than at fasting.

Figure 4:
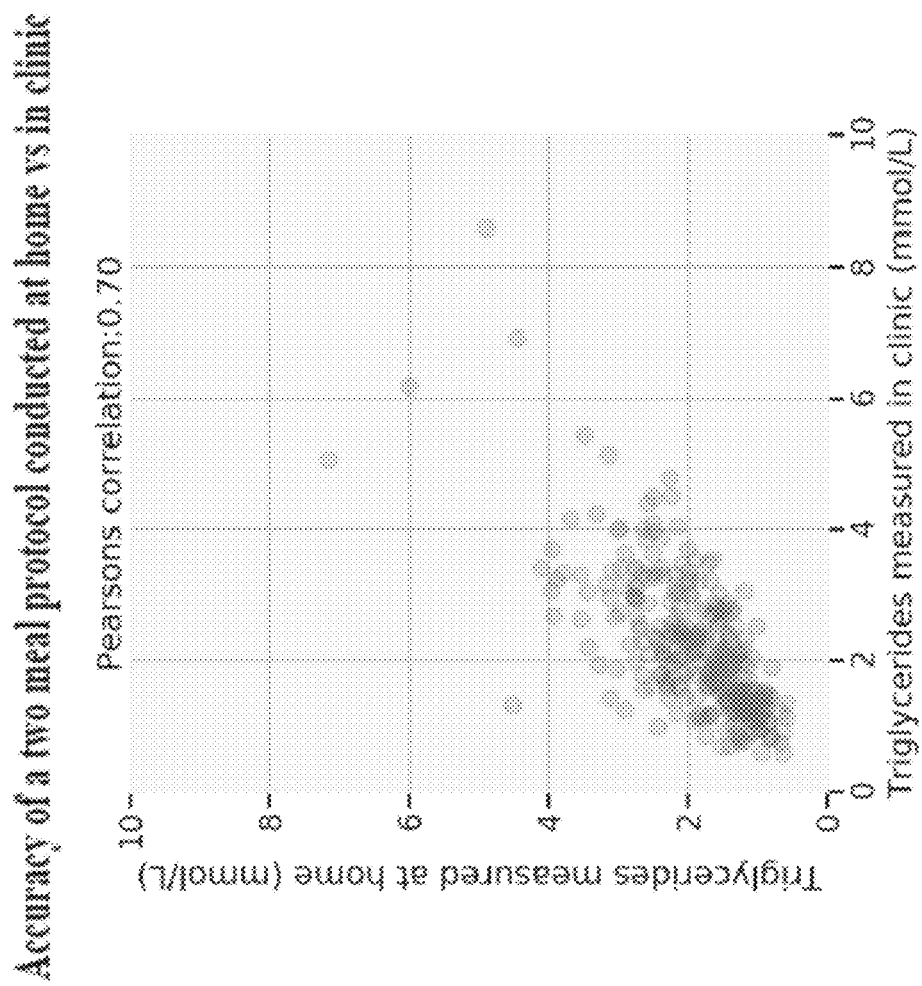
FIG. 4 shows an accuracy of a two meal protocol conducted at home vs in clinic.

FIG. 4 demonstrates that there is a good correlation between at home measurement of variation in lipid response and that seen for exactly the same individual eating a high fat meal followed by a second meal in the controlled clinic setting.

As illustrated, FIG. 4 shows the venous measurement of triglycerides in the hospital environment vs an at home blood collection measurement (dried blood spots in this particular example) of triglycerides at home for the same individual. The measurements are taken on separate days. Both measurements were taken at 5 hours after the participants had started the protocol. consisting of a fat breakfast at 0 hours and then lunch at 4 hours. This figure demonstrates that there is a good correlation between these two measures, and therefore that a two meal protocol at home gives repeatable data about triglycerides responses and is not overwhelmed by noise.

Figure 5:
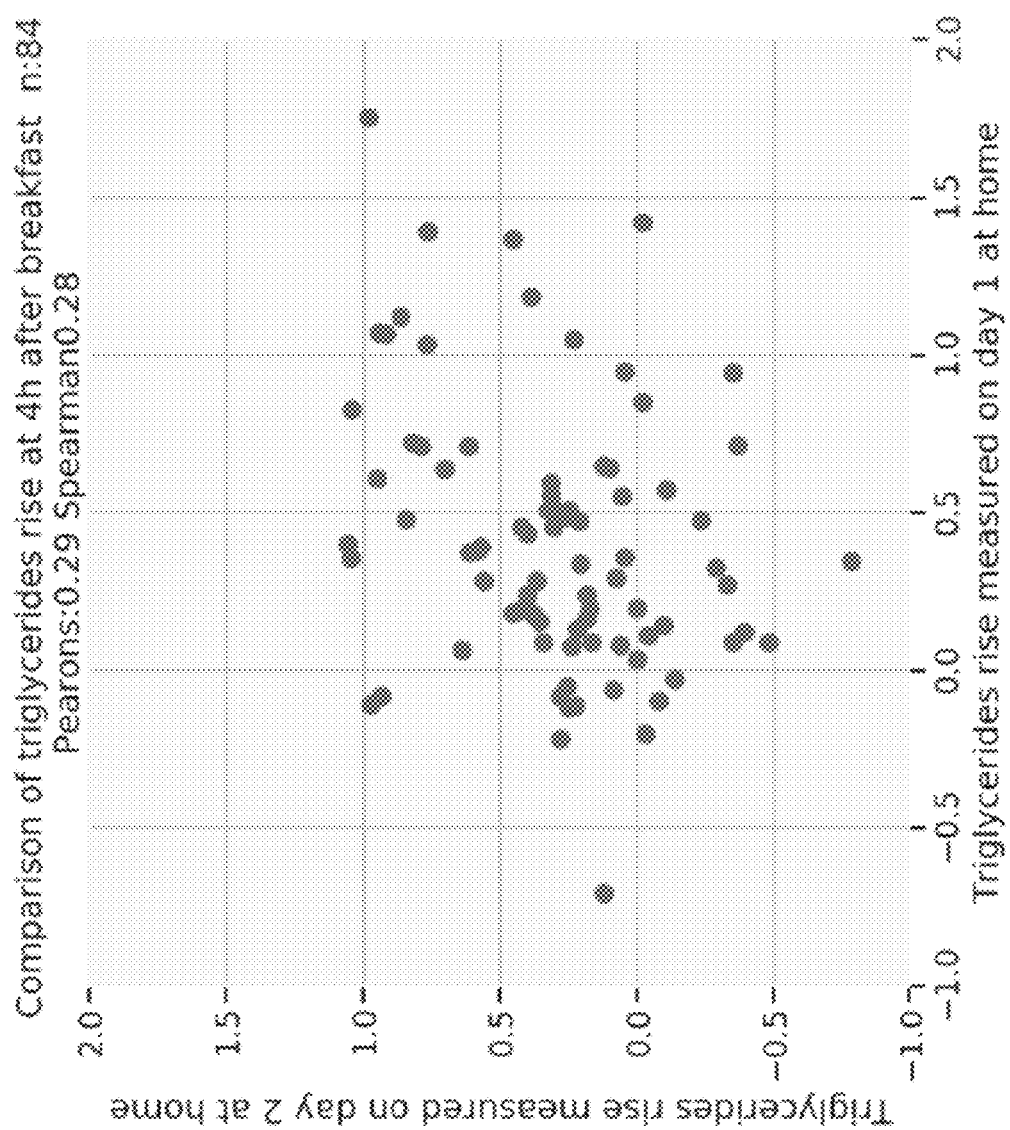
FIG. 5 shows a repeatability of a one meal protocol conducted at home on different days.

FIG. 5 demonstrates that the repeatability of a one meal protocol conducted at home on different days is much weaker than if a two meal protocol is used. This information allows us to use the data collected at home after eating a meal or series of meals to understand individual variation in lipid responses and therefore improve the accuracy of models that are used to predict clinical states and/or to predict individual responses to food such that guidance can be given on what is the right food to minimize health risks or improve an existing condition such as diabetes or cardiovascular disease.

As illustrated, FIG. 5 shows the triglycerides rise measured with at home blood collection measurement (dried blood spots in this particular example) 4 hours after breakfast on 2 separate days. A very weak correlation between the 2 measurements can be seen. This is contrast with FIG. 4 where a strong correlation was found between the clinic measurements and the home measurements of the triglycerides when a 2 meal protocol is followed.

It is possible to measure many lipids including remnant lipoproteins (RLP) at home by using at home blood collection. From around four hours after a high fat meal, the lipoprotein components of the aggregate triglycerides that is measured will have remodeled leading to remnant triglyceride rich lipoproteins and an increased number of atherogenic lipoproteins.

It transpires that the levels of these RLP post-prandially are not well predicted by levels of fasting blood results alone such as cholesterol (see FIGS. 6A-6D), and that fasting triglycerides gives a much better prediction than cholesterol. This means that approaches relying on fasting blood results are less able to model health risks affected by RLP, and therefore guidance they give on managing health risks or improving conditions are less well personalized to the individual.

However, FIGS. 6A-6D also demonstrates that by having a person undertake a high fat test meal at home and measuring triglycerides levels post-prandially a very high quality prediction of the levels of RLP can be made. By taking at-home post-prandial measurements it is possible to improve on a model built on fasting bloods and therefore improve the guidance given to individuals.

In some cases, measuring post-prandial measures like triglycerides at home will be cheaper than measuring RLP directly. Alternatively, the person can undertake a high fat meal test at home and one can measure RLP levels directly for example by collecting liquid blood using an at-home collection device and having it assayed using NMR techniques. Given the role of RLP in inflammation and its impact on long-term health risks, by adding this ability to predict or directly measure postprandial RLP responses it is possible to improve prediction of current health states and future health risks.

According to some configurations, the Lipid responses can be used to predict food responses, but also to measure risks of CVD, fatty liver disease, and a whole range of metabolic disease including diabetes.

Measuring post-prandial lipids is just one example of an at home measurement. There are many other examples of at home measurements such as using a CGM with one or a series of different test meals, or measuring the response to an OGTT (Oral Glucose Tolerance Test) in addition to the lipid test described above. In other examples, one would combine blood taken at fasting (sometimes called a baseline blood) as is often done for medical tests alongside some sort of measurement of a post-prandial response, which could be a glucose response, a lipid response, or something else.

As illustrated, FIGS. 6A-6D compare the prediction performance of two models that predict the remnant lipoproteins (RLP) in blood 6 hours after a fat meal (protocol as in FIG. 2). By adding postprandial responses into the model the accuracy of the predictions of RLP are significantly improved. Similar results were also observed with predicting RLP at 4 hours after a meal. This data is on 486 individuals undergoing the same meal as in FIG. 2. RLP was measured in all these individuals.

Figure 6A:
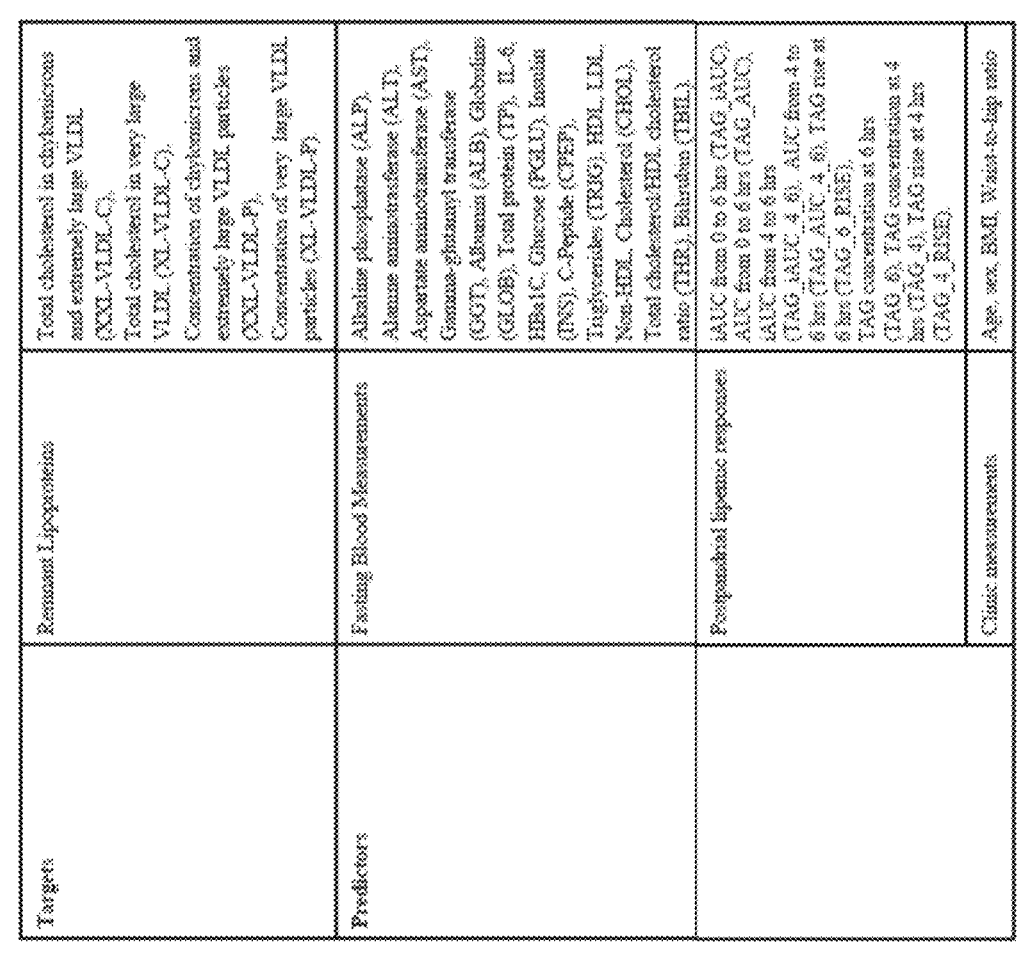

The first model predicts the remnant lipoproteins using an extensive number of predictors including fasting blood measurements and clinic measurements illustrated in the table of FIG. 6A.

The second model adds a small number of postpandrial triglycerides responses shown in the table of FIG. 6A. In some examples, linear regression with log-scaled standardized inputs to predict each of the remnant lipoproteins at 6 hours was utilized. Predictions were compared to the measured values in terms of coefficient of determination (Rsquared).

Figure 6B:
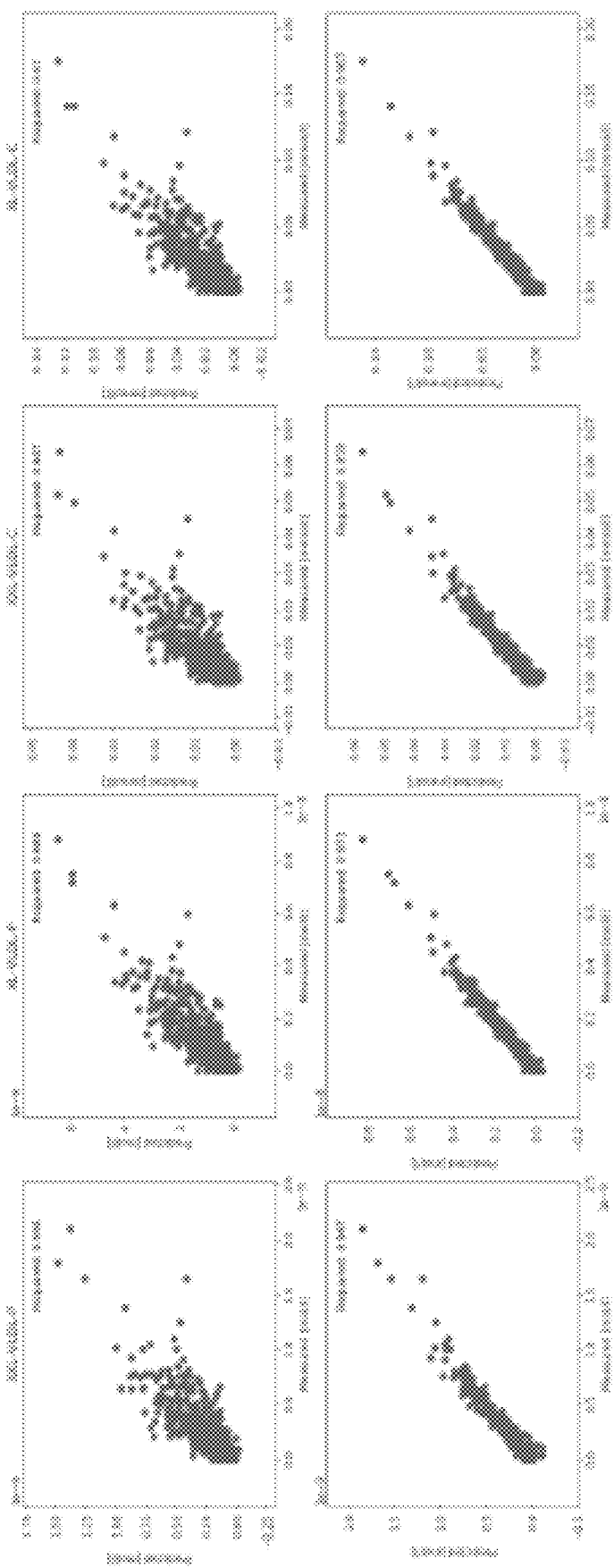

The charts illustrated in FIG. 6B show the differences in prediction performance between these two models. In the top row, scatter plots display the predicted vs measured of the remnant lipoproteins for the first model—without postpandrial lipemic responses. Plots on the second row show the corresponding predictions for the second model—with postpandrial lipemic responses. From these scatter plots and their associated R-squared values, it can be concluded that the model with postpandrial response has a significantly stronger association with the remnant lipoproteins than the models without.

Figure 6C:
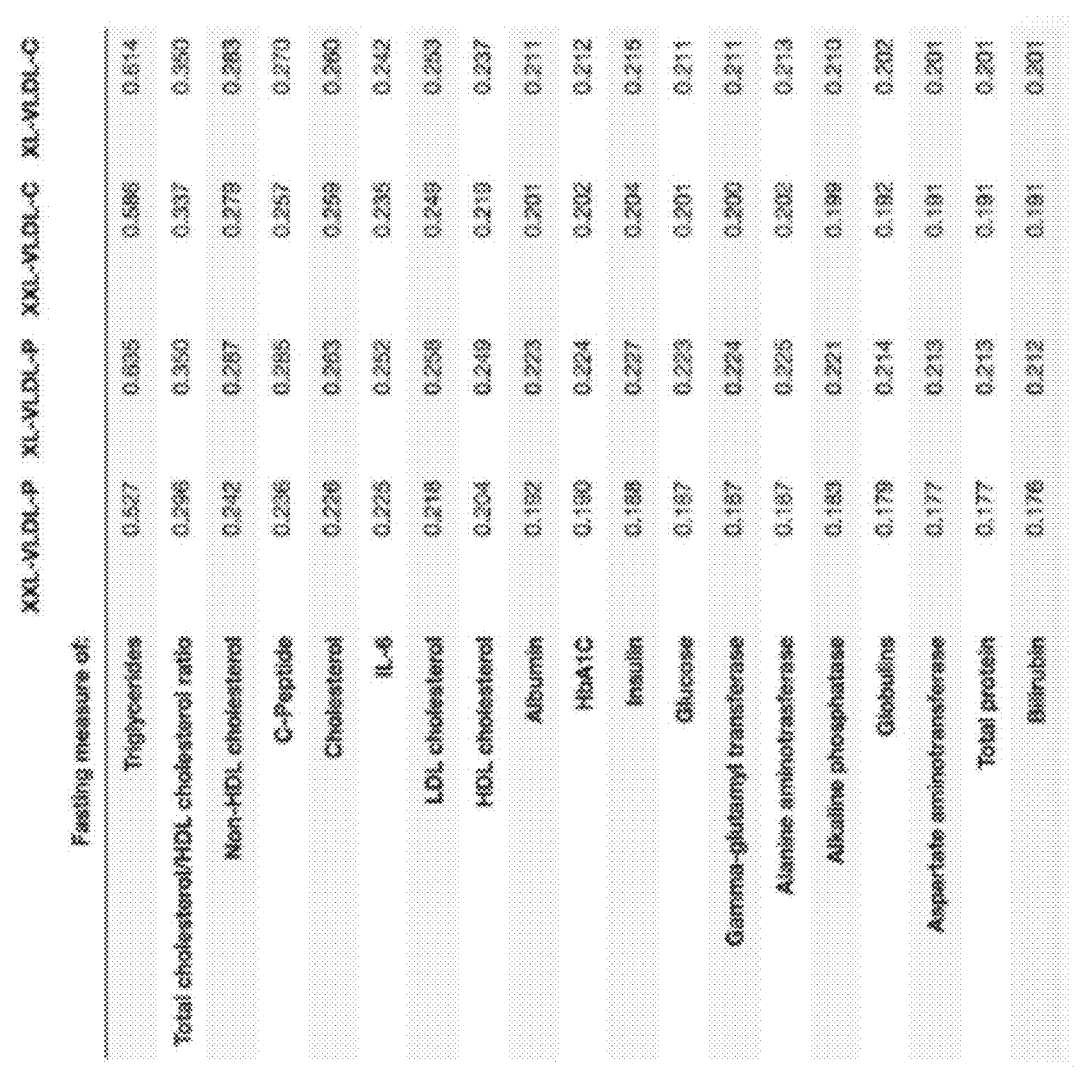

Correlation of RLP with single fasting measures—FIG. 6C illustrates which fasting blood measurements have the highest contribution to the prediction of remnant lipoproteins at 6 hours. As the table shown in FIG. 6C illustrates, fasting triglycerides contributes more than 50% to explaining the concentration of extremely large VLDL and cholesterol carried by these lipoproteins and more than 60% in very large VLDL. Cholesterol measures explain less than 25% of the RDL. It can be seen that the coefficient of determination (Rsquared) for each single fasting blood measurement to predict the remnant lipoproteins. A conclusion may be made that no single measure at baseline other than triglycerides explains a large amount of the RLP at 6 hours.

Impact of single postpandrial measure on predicting RLP—In some examples, the same analysis for every postpandrial lipemic response and observe that TAG concentration and rise at 6 hours individually explains more than 75% of the variance in the concentration of the different remnant lipoproteins, which is even higher than all baselines combined (see FIGS. 6A-6C). The table of FIG. 6D shows the coefficients of determination when predicting the remnant lipoproteins from different postpandrial lipemic responses.

In some examples, one would measure or predict protein Glycosylation (GlycA), which is a marker of inflammation predictive of cardiovascular risk. As with RLP, one can either measure this directly or predict it with other postprandial measurements such as triglycerides.

Figure 7A:
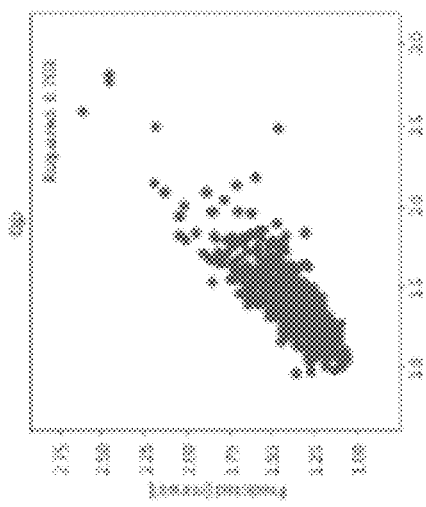
FIGS. 7A and 7B show predicting Glyca (GP) levels with and without postprandial information.
Figure 7B:
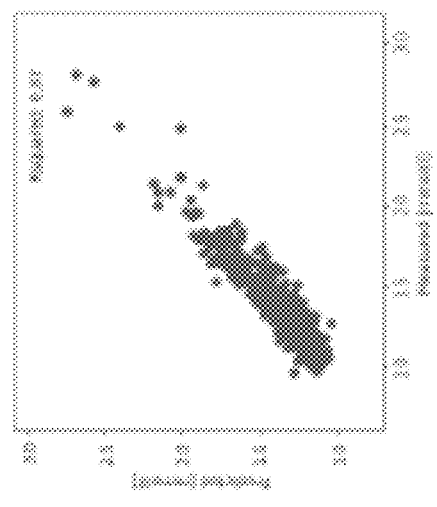

FIGS. 7A and 7B show that by having a person undertake a high fat meal test at home and measuring triglycerides levels post-prandially it may be possible to generate a significantly better prediction of the levels of GlycA compared to using fasting levels alone. Given the role of GlycA in inflammation and its impact on long-term health risks, by adding this ability to predict or measure postprandial GlycA responses it is possible to improve prediction of current health states and future health risks.

FIGS. 7A and 7B follow the same approach as described with reference to FIGS. 6A-6D to predict the level of glycoprotein acetylation, an inflammation marker that has been shown to be predictive of cardiovascular disease (CVD), heart attacks and type 2 diabetes. This protein has also been measured at 6 hours after the first meal. Again, the lower chart 720 illustrated in FIG. 7B with the addition of post-prandial triglycerides responses shows a significantly better association than the higher chart 710 in FIG. 7A which has all the baseline measures but no post-prandial responses.

The diagnostic can then combine data from multiple measurements and use machine learning to correlate these with clinical outcomes to improve prediction of one or more clinical states or to predict risk of a disease risk/health outcome (e.g. % risk of cardiovascular disease over the next decade). A very simple example is getting a traditional baseline blood assay from blood collected at home which might give readings for say 10+ different biomarkers (triglycerides, glucose, cholesterol, etc.) plus one dynamic measure (e.g., a post-prandial glucose reading after a set meal). This data can then be combined with readings of a large number of other people and provided to a machine learning mechanism, or utilizing some other technique, to generate a prediction based on the aggregated data rather than just using a single biomarker like cholesterol or HbA1c as is commonly used today as a diagnostic. The more people in the dataset the better the prediction. If the data includes other information about the individual, such as racial background, sex, weight, current medication, etc. then given enough people in the dataset it would be possible to generate a diagnostic that is more accurate for people with particular backgrounds, such as those with African-American heritage, or using particular drugs. In some cases, this diagnostic would predict a particular clinical state is likely, while in others it will be a prediction of long-term health risk for one or a series of health outcomes.

In some configurations in order to predict current disease state, the test dataset for the model includes participants with that disease state, or who go on to be identified after the event as having that disease state. By training the model with those individuals, who have undergone some or all of the tests that are carried out on the individual, it increases the accuracy of the model in identifying those disease states compared to traditional approaches that often use a single biomarker to identify a population at risk. In some configurations this allows a model to predict a current disease state based on at home tests without needing to use the same tests as are carried out in the clinic.

In some configurations in order to predict disease risk, the test dataset for the model includes individuals with known disease risk scores calculated from currently validated algorithms. In some of these configurations, which may rely on data that cannot be collected on all individuals. In some configurations in order to predict disease risk there are individuals who are seen to develop the disease at a later time from the period where their measurements are taken. By training the model with those individuals, who have undergone some or all of the tests that are carried out on the individual, it increases the accuracy of the model in identifying those disease states compared to traditional approaches that often use a single biomarker to identify a population at risk.

The use of a postprandial response improves the accuracy of the diagnostic where it is useful to measure the metabolic response of the individual. In many cases of disease, the problem is much more apparent when the metabolism is stressed and standard pathways are unable to function as normal, as during the fasting state when the body has often found a way to compensate for the problem. Thus, dynamic responses such as insulin, glucose or RLPs may respond differently between the healthy and those who are succumbing to a disease but are not yet easily identified with traditional clinical measures.

Lipid response data, and glucose response data obtained in some experiments provide evidence of this use of the data in this uncertain science area. For example, instead of using a single meal, the at home diagnostic uses two meals to diagnose a health outcome. This has been found to be useful for lipids of which there are very many—triglycerides is the aggregate name for a number of lipids.

The data from at home users, can be collected over time thereby building a large data set that can be used in the generation of predictions and determination of one or more clinical states, or health risk outcomes. A machine learning mechanism can utilize a plurality of different biomarkers to generate the predictions of clinical state/health risk outcomes. For example, the data from one user can be compared to data obtained from other users. As discussed in more detail below, data associated with a circadian rhythm (e.g., sleep times, awake times) can be utilized to improve the accuracy of the measured biomarkers.

The measured biomarkers can include many different types of health data such as microbiome data which may be referred to herein as "biome data", blood data, glucose data, lipid data, nutrition data, wearable data, genetic data, biometric data, questionnaire data, psychological data (e.g., hunger, sleep quality, mood, . . . ), objective health data (e.g., age, sex, height, weight, medical history, . . . ), as well as other types of data. Generally, "health data" can refer to any psychological, subjective and/or objective data that relates to and is associated with one or more individuals. The health data might be obtained through testing, self-reporting, and the like. Some biomarkers change in response to eating food, such as blood glucose, insulin, c-peptides and triglycerides and their lipoprotein components.

To understand the differences in nutritional responses for different users, dynamic changes in biomarkers caused by eating food such as responses to one or more standardized meals ("post-prandial responses") may be measured. To increase the accuracy of data associated with measurements in a non-clinical setting, systems can be utilized to analyze the data, to adjust the data. The systems can include computing devices (remote and/or local) and/or individuals authorized to analyze and adjust the data.

It has been found in a clinical setting (using venous blood and clinical biochemistry assays and is therefore very accurate) that the average levels of triglyceride rise little at four hours even after a very high fat breakfast (e.g., consuming a high fat muffin containing 50 grams of fat for breakfast after 12 hours fasting). However, by adding a second meal (e.g. another 22 grams of fat) average levels of triglyceride rise dramatically one hour after the second meal and begin to fall at two hours. Individual variation can be observed (even before the second meal), but the individual variation appears to be higher after the second meal. Since one measure of health implications is the absolute rise in triglycerides and whether they remain high after a meal, it can be hard to differentiate most individuals after a first meal, but in this experiment, it becomes much easier to differentiate responses by looking at the triglycerides levels at 5 and 6 hours. As such, in some examples, a second meal is added in order to better understand an individual's responses to fats in a meal.

These results appear to hold with differing levels of fats in the meals, and changes in the exact timings between the two meals. They also appear to hold if more than two meals were provided.

In some configurations, to measure the dynamic responses to meals of lipids such as triglycerides at home, the user can be given at least two set meals. According to some examples, the first meal is a breakfast after fasting and the second meal is several hours later. The first of these meals contain fat, and the second may also contain fat. The at-home measurement process can involve one measurement at fasting before eating the breakfast and at least one measurement after the second meal. It is possible to take multiple measurements (e.g. one hour and two hours after the lunch) to better characterize the response curve of the individual's lipids to this "challenge meal". Dried blood spots are one mechanism that can be used to measure these lipids at home, but any blood collection method (or other method to reliably measure lipids) could be used. In some examples, a device, such as a smartphone, can be used to remind the user to eat the lunch at precisely the right time after the breakfast and to remind them to measure their lipids at the appropriate times.

According to some examples, users can consume multiple set meals to measure one or more other biomarkers which is relatively slow moving (i.e. does not return to baseline within 2-3 hours) and where the second meal accentuates the response underway from the first meal by increasing the overall stress on the person's biological systems.

Since biological systems are designed to maintain homeostasis, it is attempted to try and disturb these systems in order to measure how rapidly the biological systems can return to their starting equilibrium and how far away the biological systems move from this equilibrium under a given pressure. It turns out that a second meal appears to be very effective at differentiating people who easily return to equilibrium and those whose systems are much more disturbed before this happens. It also appears to be a realistic measure of many people's normal state since most of us spend much of the day having had two or more meals since we woke up. This information can be used to improve the prediction of current disease state or future disease state since these dynamic measures expose problems that tend to be hidden with fasting baseline measures. By combining the dynamic measure with other measures and feeding them into a prediction model which has a large number of inputs more accurate predictions can be made than have been done using traditional risk scores which rely on a small number of static measures (often simple measures like age and BMI combined with one or two fasting blood measures such as HbA1c or HDL/LDL). In this configuration, the model's quality is improved by not only using a dynamic measure but also taking the information from many fasting measures rather than choosing to select only one or two and ignoring the information from the other measures.

Inflammation markers such as IL-6 are an example, where responses are even slower to return to baseline than triglycerides. In these examples, the meals are set meals with known levels of nutrients so that responses can be accurately compared between individuals because they are eating the same meals with the same timings between the different meals. In some configurations, Meals are eaten rapidly (e.g. within 10 or 15 minutes) to help ensure nutrients arrive at approximately the same times across individuals.

Specifically, for triglycerides if one takes three measurements of blood at home, then this means the blood spots can be taken at fasting and 1 and 2 hours after the second meal (or some other timing). If only two measurements are taken, then fasting and a timepoint somewhere between 1 and 2 hours after the second meal that is the same for all users.

In some configurations, data associated with meal timing, sleep and circadian rhythm for users is monitored. Generally, circadian rhythm refers to the 24-hour cycle that tells our bodies when to sleep, rise, and eat. In some configurations, circadian data is measured/monitored in a non-clinical setting. The circadian data can include but is not limited to sleep data (e.g., sleep times, awake times), Heart Rate ("HR") data, and the like. The circadian data can be measured by at home electronic data collection devices, and/or determined using other mechanisms. Today, these electronic data collection devices can be used to accurately measure sleep/wake times, HR, and the like for an individual. This circadian data for an individual can then be used to improve the accuracy of predictions and to predict responses at certain times of day or given a certain amount of sleep.

Obtaining this sleep and eating timing data in a clinical setting is not performed often due to the very high costs of carrying out such studies. As a result, there are very small study sizes of chrono nutrition. Chrono nutrition generally refers to the timing of meals in view of the differing responses to the same meal at different times, which may be influenced by the circadian rhythm associated with an individual, the amount of sleep they have had, when they woke up, how long since they last ate, etc. A disruption in circadian rhythm has been associated with metabolic syndrome, obesity, cardiovascular disease, and cancer. Alterations in timing of meals may also increase the risk of metabolic diseases.

It was not known how much variation there was in biological responses for individuals eating meals at different times of day outside of the clinic. However, FIG. 8 demonstrates that there is a significant variation in how individuals respond to the same meal at breakfast and lunch, with most individuals having a much larger glucose response to the meal at lunch after having the same meal at breakfast. Furthermore, the ratio between these two meals is not constant, demonstrating individual variation between these relationships. This variation can be predicted in order to provide individual guidance on the impact of meal timing and circadian rhythm on biological responses to food.

FIGS. 8A, 8B, and 8C illustrate data associated with 460 participants that ate a standardized muffin meal for breakfast and the same meal again at lunchtime. Each meal contained 71 g Carbohydrate, 22 of Fat, and 10 g of Protein. The meals were then repeated on another day. Their glucose response (incremental Area Under the curve) varied as illustrated. Chart 810 of FIG. 8A shows a meal response for breakfast and lunch. FIG. 8B shows a table 815 for breakfast and lunch. Chart 820 shows a breakfast/lunch response.

In almost all case the breakfast response was less than the lunch response, as shown in chart 820 of FIG. 8C, but there is a wide range of individual variation, which could be predicted in order to provide individual guidance on the impact of meal timing and circadian rhythm on biological responses to food.

In some configurations, a data service can utilize the circadian data (e.g., sleep data) and/or meal timing data about a user and/or many different users in determining the impact of the body clock, sleep duration and quality and the timing of previous meals on how a user will respond to food. For instance, when a user is determined to have disrupted their sleep cycle, a data service can perform an action (e.g., adjust the data) to adjust for the disruption in the circadian rhythm. In other examples, the data service can adjust the data for one or more measured biomarkers based on the circadian data (e.g., the time of day, how much sleep the user had, . . . ). This better allows meal data to be combined, for example if they were eaten at different times of day, or on days with more or less sleep than normal, or where the meals followed different earlier meals in the day. The data service can also utilize a data analyst, a machine learning, and/or some other mechanism to adjust the as well as providing the data to one or more other services, for predictions, recommendations, and the like.

In some examples, circadian data and/or meal timing data is provided to one or more machine learning mechanisms. As a result, the predictions of biomarker responses to a meal can respond to the time of day, the user's normal circadian rhythm and previous meals so as to better predict the actual response that will be seen to a meal. These predictions can be used to generate nutritional recommendations to users that allow them to understand the effect that the time at which they eat a meal will have on their response to that meal, as well as the effect of disrupting their circadian rhythm or changing the amount of sleep they have or when they wake up. In other examples, or as a way to provide training data to the computing systems using a machine learning mechanism or some other technique, a data analyst viewing the received data may utilize different tools (electronic and/or non-electronic) to interact with the timing data. For example, as described in more detail below, one or more user interfaces may be utilized by a data analyst to review and adjust the data. The ("UIs"), such as graphical user interfaces ("GUIs"), can include user interface elements that are utilized by the data analyst to review the data, compare the data of the user with other data, and the like.

According to some examples, stool collection and microbiome analysis can be utilized to predict post-prandial blood fat levels. In some configurations, stool collection, metagenomics analysis, measurement of post-prandial responses can be utilized in an at-home and/or clinic setting (as covered herein and in the referenced applications) and machine learning that can take a stool collected at-home and use this to predict the responses of blood fat levels to different meals. Previously, it was uncertain that this could be done, because biology is an uncertain science and it was not known whether the gut microbiome (which is not part of the human body but is a changing ecosystem of bacteria influenced by and influencing the host body) can be used as an indicator of the individual's responses to fatty meals.

Figures 10A, 10B:
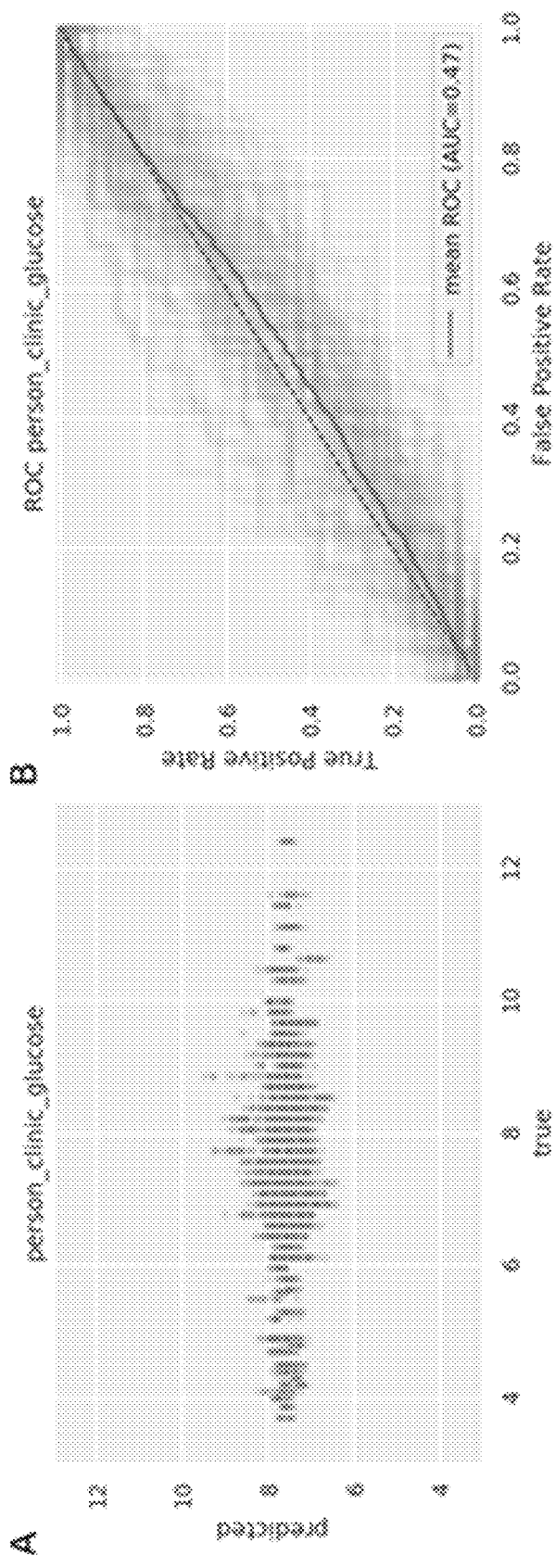
FIGS. 10A and 10B illustrate example results of two machine learning models: a regressor and a classifier approach in predicting the glucose baseline levels.

FIGS. 9A and 9B demonstrate that this data can be used to predict post-prandial blood fat levels with significant accuracy as demonstrated by the correlation coefficients, whereas FIGS. 10A and 10B indicate that this data does not work well for measuring glucose responses as demonstrated by the correlation coefficients despite some prior claims to the contrary.

The accuracy of these machine learning predictions of post-prandial blood fat levels can be enhanced by using the data gathered from the microbiome as an input into the systems described herein, and in the referenced applications, and this data can be used to improve the food recommendations described therein.

The microbiome can be defined as the collection of microorganisms (bacteria, fungi, viruses, and micro-eukaryotes) that live in and on the human body. One method by which the human gut microbiome, in particular, can be studied is by collecting stool samples from which all the DNA material is extracted and sequenced using a high-throughput platform to get the genomes of the microorganisms. This technique is called metagenomics and allows one to assess which microbes are present in the sample, without cultivation intensive efforts, such as isolation of every single species present in a microbiome. Metagenomics, moreover, solves the problem of surveying of those microbes that cannot be cultivated and isolated in a laboratory.

The data from a metagenomics high-throughput sequencing is a large set of millions of stretches of short DNA fragments (reads) that all together are called a metagenome and are a representation of a microbiome sample. A primary analysis of a metagenome is the taxonomic and abundance profiling, which aims to indicate which microorganisms are present and at what relative abundance. There are several approaches available to perform taxonomic profiling, but the one minimizing the false positive ratio is a marker based one. A marker-based profiler is highly accurate in determining which species are present in a metagenome because it exploits species-specific markers that can be pre-computed exploiting the large availability of genomes in public databases.

One approach is to use the taxonomic profile to predict human biomedical measures, and this, in turn, is showing that the microbiome can be used as a non-invasive way to estimate human health. This can be used to predict post-prandial responses of various metabolites in the blood such as triglycerides and its components (HDL, LDL, remnant lipoproteins, etc.).

In some examples, a machine learning model is built using this data and/or other data described herein and in the referenced applications. One approach is that the machine learning regressor has the aim of predicting the triglyceride level values of the people using the relative abundance of the microbiome species profiled, which can be done by ensuring these individuals are given a standardized meal that can differentiate their fat responses sufficiently for this to be clearly measured, as described herein and in the referenced applications.

In an attempt to verify that this can be done in human beings, data was collected and taxonomic profiling carried out on ~500 human gut metagenomes generated from stool samples from participants in the PREDICT 1 Study, and this data was combined with measured post-prandial responses for each of these individuals. The microbiome data was then used as input features for both a machine learning regressor and classifier. The machine learning regressor employed in this particular analysis has the aim of actually predicting the triglyceride level values of the people using the relative abundance of the microbiome species profiled. For the classification approach, the data was converted into two classes by dividing the dataset into low-triglyceride (the lower quartile of the distribution) and high-triglyceride (higher quartile of the distribution) classes. Then a machine learning classifier was employed to classify people based on their microbiome composition into the two defined classes. More classes may be utilized. Similarly, other scoring mechanisms can be utilized.

It was found that triglyceride levels at 6 hours after the baseline measure may be confidently predicted. As such, at least in some examples, microbiome can be utilized to estimate also other biomedical relevant post-prandial measures for humans.

The example of FIG. 10. demonstrates that microbiome cannot predict well all post-prandial responses, and that prior to carrying out this biological study it was not possible to know whether microbiome could be used to predict post-prandial lipid responses.

FIG. 9. illustrates example results of the two machine learning models: a regressor and a classifier approach in predicting the triglycerides levels at six hours. The two panels in FIG. 9 report the results of the two machine learning models in predicting the triglycerides levels at six hours after breakfast. The breakfast meal is followed by lunch after two hours. (A) Result of the machine learning regressor model, with a median Pearson correlation coefficient of 0.246. (B) Result of the machine learning classifier showing a median Area Under the Curve of the Receiver Operating Characteristic curve of 0.719 with a Matthews correlation coefficient of 0.266.

FIG. 10 illustrates example results of the two machine learning models: a regressor and a classifier approach in predicting the glucose baseline levels. The two panels in FIG. 10 report the results of the two machine learning models in predicting the glucose baseline levels measured before breakfast. (A) Result of the machine learning regressor model, with a median Pearson correlation coefficient of −0.009. (B) Result of the machine learning classifier showing a median Area Under the Curve of the Receiver Operating Characteristic curve of 0.47 with a Matthews correlation coefficient of −0.063.

Additional details regarding the various components and processes described above will be presented below with regard to FIGS. 11-15.

It should be appreciated that the subject matter presented herein may be implemented as a computer process, a computer-controlled apparatus, a computing system, or an article of manufacture, such as a computer-readable storage medium. While the subject matter described herein is presented in the general context of program modules that execute on one or more computing devices, those skilled in the art will recognize that other implementations may be performed in combination with other types of program modules. Generally, program modules include routines, programs, components, data structures and other types of structures that perform particular tasks or implement particular abstract data types.

Those skilled in the art will also appreciate that aspects of the subject matter described herein may be practiced on or in conjunction with other computer system configurations beyond those described herein, including multiprocessor systems, microprocessor-based or programmable consumer electronics, minicomputers, mainframe computers, handheld computers, personal digital assistants, e-readers, mobile telephone devices, tablet computing devices, special-purposed hardware devices, network appliances and the like.

In the following detailed description, references are made to the accompanying drawings that form a part hereof, and that show, by way of illustration, specific examples or examples. The drawings herein are not drawn to scale. Like numerals represent like elements throughout the several figures (which may be referred to herein as a "FIG." or "FIGS.").

Figure 11:
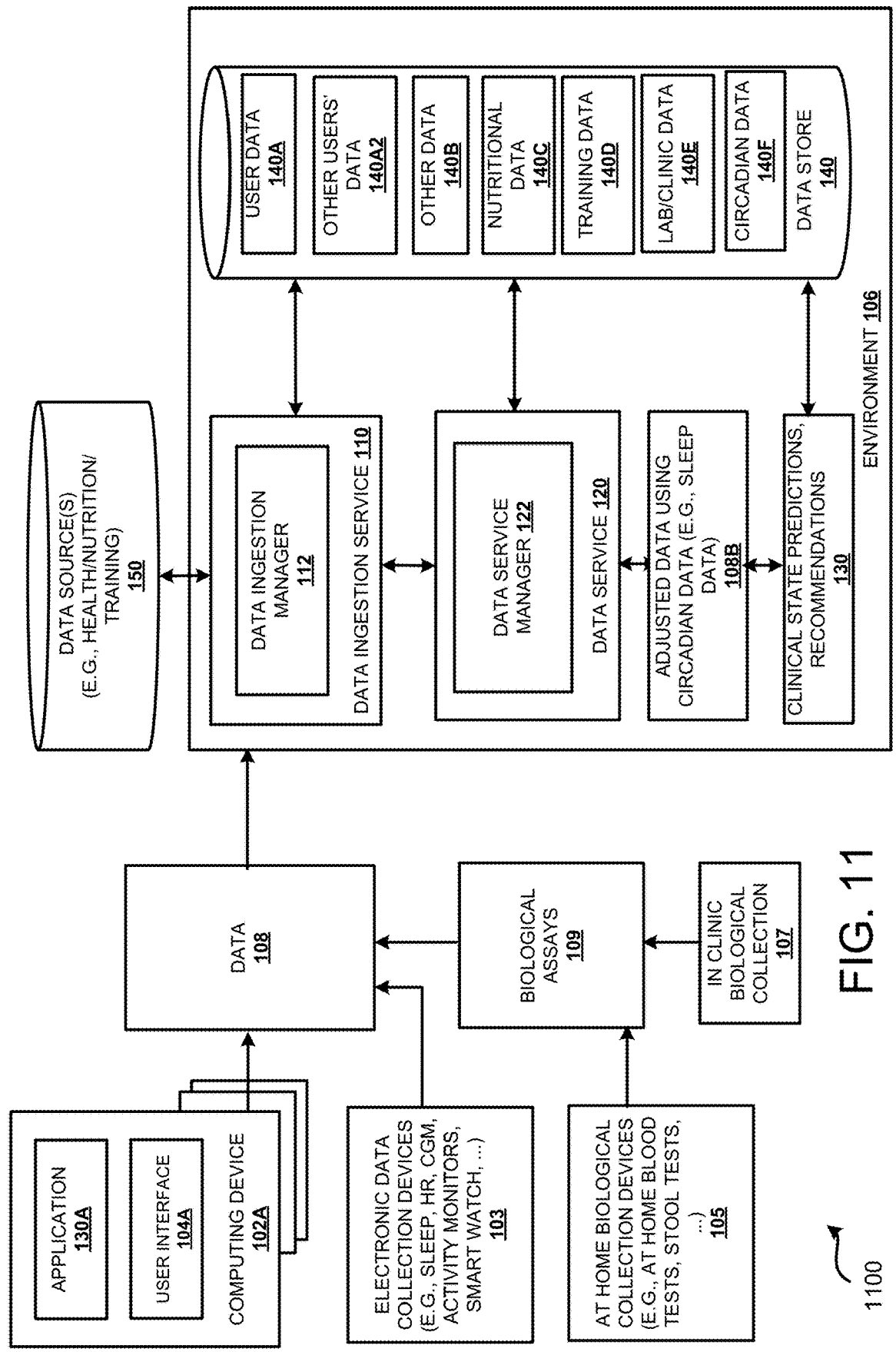
FIG. 11 is a block diagram depicting an illustrative operating environment in which at home measurements are used to predict clinical state and the accuracy of the at home measurements/predictions can be improved using data associated with circadian rhythms.

FIG. 11 is a block diagram depicting an illustrative operating environment 1100 in which at home measurements are used to predict clinical state and/or disease risks and the accuracy of the at home measurements/predictions are improved using data associated with circadian rhythms. An individual, may communicate with the environment 106 using a computing device 102 and possibly other computing devices, such as electronic data collection devices 103.

In some configurations, one or more electronic data collection devices 103 can be used to collect some of the data 108. For example, the electronic collection devices 103 could include devices configured to collect circadian data (data associated with the circadian rhythm of a user such as sleep data, HR data, activity data, . . . ), a CGM device, an activity monitor, a smart watch, and the like. These electronic data collection devices 103 may be worn on the body in which case they generate "wearable" data. For instance, an individual may wear a fitness device, such as an activity-monitoring device, that monitors sleep, motion, heart rate, blood pressure and the like and can be used to determine how much an individual has slept, the number of calories burned, activities performed, body temperature, and the like. The individual may also wear a CGM that monitors blood glucose levels often by measuring levels of glucose in interstitial fluid. New devices are constantly becoming available to individuals. For example, devices for monitoring/measuring hydration status, metabolism, physical and psychological stress, sleep, and the like are becoming more readily available. Similarly, devices for measuring biomarkers are being developed for use by an individual. Generally, an electronic data collection device 103 can include existing devices as well as devices that have yet to be developed.

In some configurations, an individual may generate and provide data 108 using a variety of at home biological collection devices 105, which collect a biological sample which requires a biological assay 109 to be performed to generate electronic data 108. These devices may include but are not limited to "At Home Blood Tests" which use blood extraction devices such as finger pricks which in some examples are used with dried blood spot cards, button operated blood collection devices using small needles and vacuum to collect liquid capillary blood and the like. In some examples there may be home biological collection devices such as a stool test which is then assayed to produce biomarker data such as gut microbiome data. Some of the data 108 may be biomarker data, such as blood glucose results collected by the CGM. Some of this data may be non-biomarker data such as photos and time stamps.

An individual may also provide data using computing device 102A. In some configurations an individual can input data 108 into one or more software applications 130A. For example, an individual may enter the food they consumed, a value indicated by a measurement device, their waist measurement and the like.

Alternatively, and/or in addition to the above, data generated by other measurements can be used to assist in determining when a food was eaten, and/or a test was performed. For example, in some cases a CGM can be used to confirm the start point of a meal. In this example, data recorded by an individual about when they started to eat can be verified by confirming that there is a rise in glucose detected by the CGM, provided there was sufficient carbohydrate in the meal.

As briefly discussed above, instead of eating a single meal once and measuring/recording the nutritional response a single time, the meal, or a different meal, may be consumed one or more additional times to improve the accuracy of the at home testing. In some examples, the repeating of the eating of the same food can be used to obtain more accurate measurements of nutritional responses as compared to eating a single meal of the food. In other examples, different meals may be consumed to increase the accuracy. The increased accuracy can also be used to generate better predictions. In some configurations, the values of the nutritional responses can be adjusted based on the circadian data.

According to some examples, two or more measurements of the same biomarker can be combined to increase the accuracy of the measurement of nutritional responses. In other examples measuring fasting bloods on more than one occasion and combining this data can be used to more accurately calculate baseline levels of biomarkers, and therefore improve calculations of nutritional responses.

As illustrated in FIG. 11, the operating environment 1100 includes one or more computing devices 102, such as computing devices 102A in communication with an environment 106. In some examples, the environment 106 may be associated with and/or implemented by resources provided by a service provider network such as provided by a cloud computing company. The environment 106 includes a data ingestion service 110, a data service 120, and a data store 140. A service 130 can be utilized to generate clinical state predictions/recommendations. For example, the personalized nutritional recommendations can be generated using techniques described in U.S. patent application Ser. No. 15/894,798, filed on Feb. 12, 2018, which is incorporated by reference herein in its entirety.

The environment 106 may include a collection of computing resources (e.g., computing devices such as servers). The computing resources may include a number of computing, networking and storage devices in communication with one another. In some examples, the computing resources may correspond to physical computing devices and/or virtual computing devices implemented by one or more physical computing devices.

The data ingestion service 110 facilitates submission of data utilized by the data service 120 and, in some configurations, the nutritional service 130. Accordingly, utilizing a computing device 102, an electronic collection device 103, an at home biological collection device 105 or via in clinic biological collection 107, an individual may submit data 108 to the nutritional environment 106 via the data ingestion service 110. Some of the data 108 may be biomarker data, and some of the data 108 may be non-biomarker data such as photos, barcode scans, timing data, and the like. Data may also be obtained by the data ingestion service 110 from other data sources, such as data source(s) 150. For example, the data source(s) 150 can include, but are not limited to nutritional data (e.g., nutrition of particular foods, nutrition associated with the individual, and the like), health data records associated with the individual and/or other individuals, and the like.

The data, such as data 108, or data obtained from one or more data sources 150, may then be processed by the data manager 112 and/or the data service manager 122 and included in a memory, such as the data store 140. As illustrated, the data store 140 can be configured to store user data 140A, other users' data 140A2, other data 140B, nutritional data 140C, lab/clinic data 140E, circadian data 140F, and the like. In some examples, the user data 140A and other users' data 140A2 includes data and health data that can include psychological data, subjective health data and objective health data. According to some examples, the data 108 is associated with at home measurements of nutritional responses to food. In some examples, data sources 150 may include training data that can be obtained from a number of individuals (e.g., >100, 500, 1000, . . . ).

This training data may be the results of at home and clinical measurements of nutritional responses using the same or different devices as used for the data 108. This training data may also include circadian data associated with a large number of users. This training data may include the results generated by using the data service 120 on the data from these other individuals, such as adjusting certain data. This training data can be provided to the data service 120 which may utilize a machine learning mechanism or other automated program to analyze the data 108 associated with an at home measurement of a nutritional response.

The data service 120 utilizing the data service manager 122 can analyze the data 108 associated with an at home measurement of a nutritional response, and then adjust the data when determined. For example, the data service manager may adjust the data 108 based on the timing of one or more tests, the circadian data, and the like. As briefly discussed above, the at home measurements may be associated with at least two different at home sources of data (e.g., combining at home CGM and at home blood measurements, or combining time recorded on a computing device with blood measurements).

In some examples, the data service 120 utilizes both data associated with the user providing the data and data from other users performing similar tests. In other examples, the data utilized is associated only with the user. According to some examples, the data can include data obtained from a clinical setting, which is typically more accurate than at home measurements. According to some examples, the data service 120 is configured to determine the level of accuracy of data for the biomarkers associated with insulin, glucose, c-peptide, ketone bodies, triglycerides, IL-6 inflammation, microbiome, hunger, fullness, mood, and the like for an individual.

In some examples, the data service manager 122 may utilize one or more machine learning mechanisms. For example, the data service manager 122 can use a classifier to classify the data within a classification category. In other examples, the data service manager 122 may generate a score that provides an indication of the likely level of accuracy of the data for one or more biomarkers.

The data ingestion service 110 and/or the data service 120 can generate one or more user interfaces, such as a user interface 104A and/or user interface 104B, through which an individual, utilizing the computing device 102, or some other computing device, may provide/receive data from the environment 106. For example, the data ingestion service 110 may provide a user interface 104A that allows an individual of the computing device 102A to submit data to the environment 106. The data service 120 may provide a user interface 104A that provides adjustments and/or instructions to the user for performing at home tests for nutritional responses.

As briefly mentioned above, instead of using a single at home test to measure one or more biomarkers (e.g., a blood glucose response) to a meal, the test/meal may be repeated more than once to measure the one or more biomarkers. In other examples, two different meals may be consumed. By combining the results from more than one test, the data service 120 can improve the level of accuracy of the calculated nutritional response. Further, the data service 120 can utilize the circadian data to increase the accuracy of the measured biomarker. In some examples, the data service 120 receives at home measurements for one or more of insulin, c-peptide, glucose, ketone bodies, hunger, energy levels, IL-6 inflammation and triglycerides. Insulin, glucose and triglycerides are metabolites that can affect body weight. The data service 120 can also be utilized with other at home measurements not specifically discussed.

While the data ingestion service 110, the data service 120, the service 130 are illustrated separately, all or a portion of these services may be located in other locations or together with other components. For example, the data ingestion service 110 may be located within the data service 120. Similarly, the data service manager 122 may be part of a different service, and the like.

In some cases, the measurements are taken by electronic data collection devices 103, such as the Continuous Glucose Monitor (CGM), that have a limited operating duration. As discussed above, data 108 can also come from other sources, such as at home biological collection devices 105, and/or in-clinic biological collection.

To provide a more complete understanding of determining nutritional responses to a particular food, an example protocol will now be described. It will be appreciated that changes can be made to the following steps and procedures.

In some examples, food item(s) selected for a particular test are standardized across different individuals. These "standardized meals" are carefully measured meals that can be packaged and eaten by the individual at home. Instructions are provided to the users to eat the meal at predefined times (e.g., after waking up without eating anything else.). In some examples, more than one meal is utilized. As will be discussed in more detail below, meals that include different nutritional ratios or composition may be included. The at home tests performed can include one or more blood tests that are taken at different points in time relative to when the meal is consumed, depending on biomarkers being measured.

If only a single meal is to be eaten, the components of carbohydrate, fat, protein ("macronutrients") and fiber are chosen to help ensure that on average there is a significant post-prandial change in the individual's target biomarkers. For example, if the target is to measure blood glucose and blood lipids, the meal will have significant carbohydrate levels (e.g. above 30 grams) and fat levels (e.g. above 20 grams.) If there are a series of standardized meals, the standardized meals can be chosen to expose the individual to a variety of meals so as to measure the interpersonal variability of biomarker responses. One example series of meal might explore a range of levels of macronutrients: (1) metabolic challenge (50 g fat, 85 g Carbohydrate); (2) high fat breakfast (35 g fat, 35 g Carbohydrate); (3) medium fat breakfast (22 g fat, 71 g carbohydrate), (4) low fat/high carbohydrate breakfast (9 g fat, 95 g Carbohydrate); (5) Oral Glucose Tolerance Test. (0 g fat, 75 g Carbohydrate). Other series of meals can be utilized. For example, another series of meals might explore different sorts of macronutrient composition such as varying type of carbohydrates with differing levels of processing (e.g. a bread using highly refined flour vs unrefined rye bread).

Not all meals provide the same amount of incremental information about a meal. For example, once the results of an Oral Glucose Tolerance Test ("OGTT") have been measured then the incremental information from a high carbohydrate breakfast made of processed carbohydrates may be small. The test series of meals may therefore be optimized to choose a set of meals that provide additional incremental information about personalized responses to food based on measuring the incremental information gained from different meals eaten by many individuals who have already had their responses measured. In some cases, the data service can choose a combination of standardized meals that is optimized for an individual that provides insight into the individual's responses within the limitation of a certain number of standardized meals.

In other examples, insulin post-prandial responses can be calculated by modelling insulin levels via c-peptide levels from at home blood measurements. C-peptide is released into the blood as a byproduct of the formation of insulin by the pancreas. A c-peptide test measures the amount of c-peptide in a blood or urine sample. Post-prandial c-peptide response can be used to provide an estimate of the insulin response. According to some examples, the accuracy of the at home measurements can be enhanced by lab/clinical measurements on the same user or other users using some combination of the same at home testing method and/or higher accuracy clinical assays.

Nutritional responses to these meals can be measured using one or more tests. In some examples, At Home Blood Tests can be utilized to not only identify the post-prandial response to these individual meals but may also be utilized to predict responses to meals that were not measured by for example building a model linking biomarker responses to the characteristics of the meal. This model can be implemented within a nutritional service 130 as described herein.

As discussed briefly above, the standardized meals may be repeated. Given the high degree of noise inherent in measuring nutritional responses at home, this increases accuracy by having multiple measurements of biomarker responses to the same meals which may be statistically combined to generate a more accurate measure of the individual's response to a particular meal. This may be done using the data service 120.

In some examples, very high fat meals are utilized to allow measurement of triglycerides responses as well as carbohydrates. In some cases, this first meal may be followed by a second meal roughly one hour—four hours after the first meal. According to some examples, the meals can be different. In some cases, this high fat meal may consist of two high fat muffins and a NESQUIK milkshake, or a similar drink. Nutrient profile: 869 kcal, 82 g carb, 55 g fat, 15 g protein, 2 g fiber. When there is a second meal it may consist of a muffin which might contain 600 kcal (75 g Carb, 25 g Fat). This is intended to (1) further differentiate triglycerides responses between individuals in the hours after this meal, and (2) elicit a second insulin & c-peptide response that can be measured during the clinical visit. It will also ensure individuals do not get hungry before the end of the clinical visit.

In order to improve the accuracy of these tests, more than one test can be combined. For instance, combining the At Home Blood Test results with other measurements such as blood glucose via a CGM may be utilized.

Post-prandial measurements can be timed to coincide with the peaks for the target biomarkers, or to measure the most relevant part of the response for understanding personalized responses. For example, measuring around one hour after eating a meal is optimized for peak c-peptide response, and around 4 hours after the meal is optimized for peak triglycerides response. In another example with triglycerides the most relevant measure may not be the peak value, but the level of triglycerides recorded beyond four hours when the lipoprotein components of the aggregate triglycerides that is measured will have remodeled leading to remnant triglyceride rich lipoproteins and an increased number of atherogenic lipoproteins. These times can be adjusted based on the particular biomarker being measured. In some examples, the timing of blood tests at home is determined based on measurement of the particular post-prandial response to that meal in a clinical setting to identify the average person's peaks for the target biomarker. In some examples an area under curve is desired to be modeled which uses at least two measures beyond the fasting measure.

If one wants to capture the post-prandial response of biomarkers which peak rapidly after meals (e.g. c-peptides), and those that peak slowly (e.g. fats such as triglycerides), then this, in some examples, uses at least three time points for blood collection on a single meal. For example, one before the meal (fasting), one measurement at around one hour after the meal, and another measurement at around four hours after the meal. This timing allows peak levels to be captured for a range of biomarkers and then compared between individuals.

The timing of tests performed at home affects how accurate are the results of the test, as many biomarkers change significantly and rapidly post-prandially. The clock used for recording the timing of the tests can be synchronized with the clock used by the CGM, and the clock used for the online food logging before the at home collection begins. This will allow the data to be accurately combined which may be done using the data service 120. If timing is inaccurate the values measured can be far from their true values. The application 130 operating on the computing device 102 can be programmed to adjust the clocks on the applications running on the device and/or data service 120 can determine the time differences between each of the clocks such that the data is correlated. As also discussed above, the data service 120 can adjust the results based on the circadian data.

According to some examples, as discussed briefly above, a Continuous Glucose Monitor (CGM) may be attached to the individual for some or all of the period they are being measured at home. This CGM may be attached by the individual themselves at home. The CGM's clock can be synchronized with the clock on the computing device 102A, usually by synchronizing both to Internet time.

By wearing a CGM it is possible to combine highly accurate glucose data with data captured by other devices. In particular this allows the measurement at home of both the glucose response and one or more other biomarkers to the same meal using an At Home Blood Test. This is beneficial since, for example, many meals that generate low glucose responses are low in carbohydrate but high in fat and it is therefore valuable to measure the fat responses in the blood in order to determine the likely health effects of such a meal rather than rely only on glucose results.

The CGM can also be used to check the timing and content of the meals. If a glucose spike is not triggered shortly after a meal that is known to lead to such spikes (for example most meals that have carbohydrates in them) then this can be used by the data service 120 to reinterpret the data from an At Home Blood Test, and either reject it or adjust for the correct starting point of the meal. The size of the spike can also help to identify the accuracy of the food logged, so for example if the glucose spike is higher than expected then this could suggest the quantity of food is more than was logged.

As insulin is not very stable once extracted, it is not a good candidate for at home measurements. To overcome this, c-peptide may be measured using At Home Blood Tests, and then the insulin level may be calculated from the value of the c-peptide. This works because c-peptide can be relatively stable over many days, especially if using dried blood tests or other blood collection methods which may be put in the fridge at home before sending them to be analyzed. To calculate insulin values from c-peptide, it is helpful to have a large benchmark of data from in clinic biological collections 107 comparing the calculated c-peptide levels using the At Home Blood Test process at the clinical visit with the known values of insulin measured very accurately using venous blood and clinical biochemistry at the same time as the At Home Blood Test process. Using this data set it is possible to take one or more c-peptide values from a user's At Home Blood Test(s) and calculate the insulin levels for that individual. This data would be further improved if that individual did a clinical visit to do in clinic biological collections 107 which would provide further data to calculate that individual's relationship between c-peptide and insulin. In some configurations, the data service 120 can utilize data received by many different users in determining whether or not a measurement is accurate. The data service 120 can utilize a data analyst, a machine learning, and/or some other mechanism to generate a quality score for the data.

The activity level of individuals can be monitored using electronic data collection devices 105 that include devices like accelerometers and heart rate measurement. These can be used to calculate exercise and sleep amongst other things. These can be used as another check by the data service 120, as for example it isn't possible to be running and doing blood tests at the same time, and it isn't a good baseline blood measurement if the individual has been awake for twelve hours or did not sleep the night before.

According to some examples, the sleep and wake times of individuals are measured at home. For instance, at home electronic data collection devices 103 can be used to accurately measure sleep and wake times for an individual. The sleep and wake times for an individual can then be used to improve the accuracy of predictions and to predict responses at certain times of day or given a certain amount of sleep. In some configurations, the data service 120 can utilize data (e.g., sleep data) received by many different users. The data service 120 can then utilize a data analyst, a machine learning, and/or some other mechanism to adjust this data 108B as well as providing the raw data to the nutritional service.

To improve the accuracy of at home measurements of nutritional responses, cross-checking can be performed by the data service 120, a support team including one or more data analysts, or some other computing device. For example, through cross-checking of various combinations of two or more of: questionnaires, photos taken by the mobile phone, food logged, CGM, At Home Blood Spot recording, activity level monitoring or other electronic data collection devices, and data recorded by the one or more data analysts a determination can be made as to whether the data is accurate. The cross-checking can be performed by the data analyst, and/or the data service. As discussed above, circadian data can be used to improve the accuracy of the measured responses.

Figure 12:
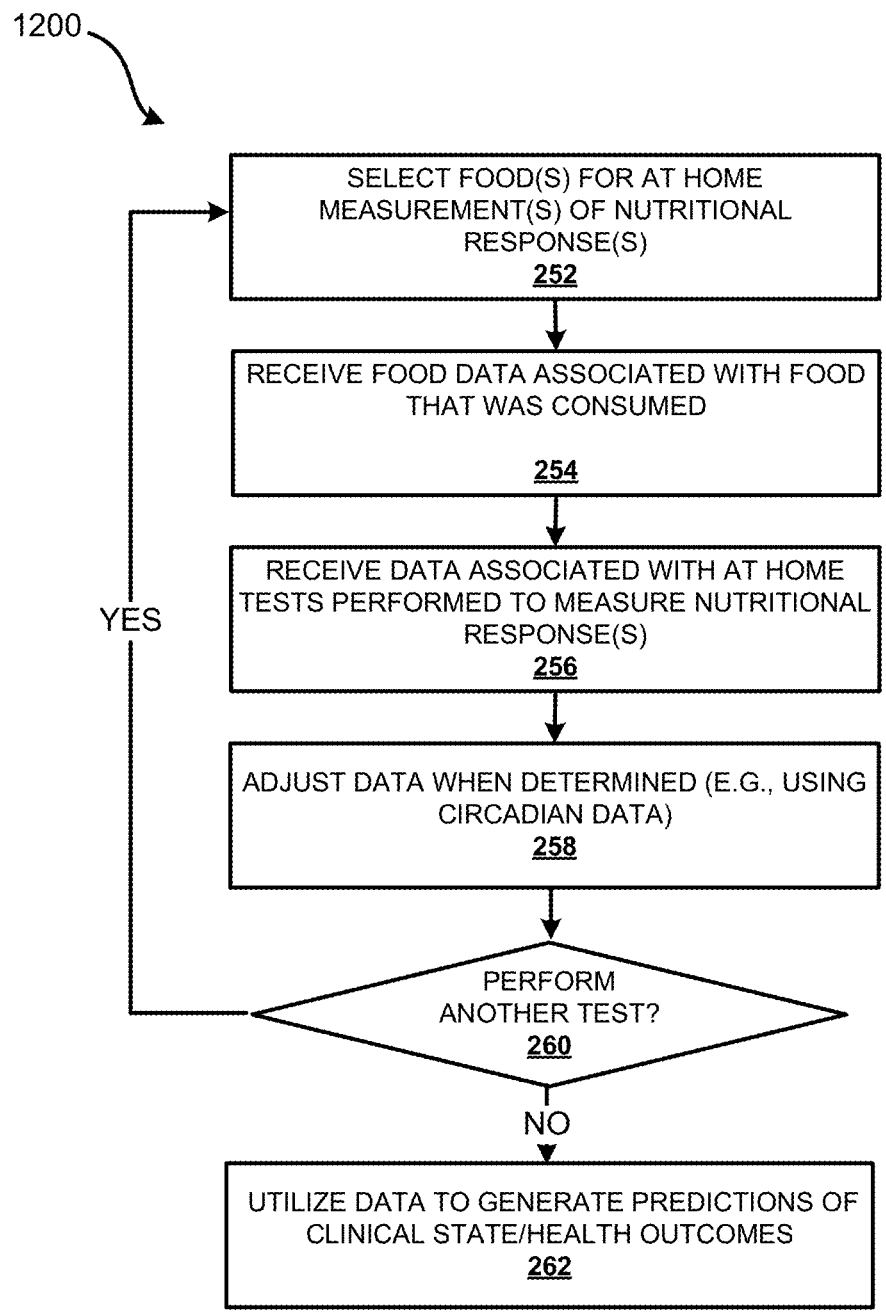
FIG. 12 is a flow diagram showing a routine illustrating aspects of a mechanism disclosed herein for generating predictions of clinical state/health outcomes using data obtained in a non-clinical setting.
Figure 13:
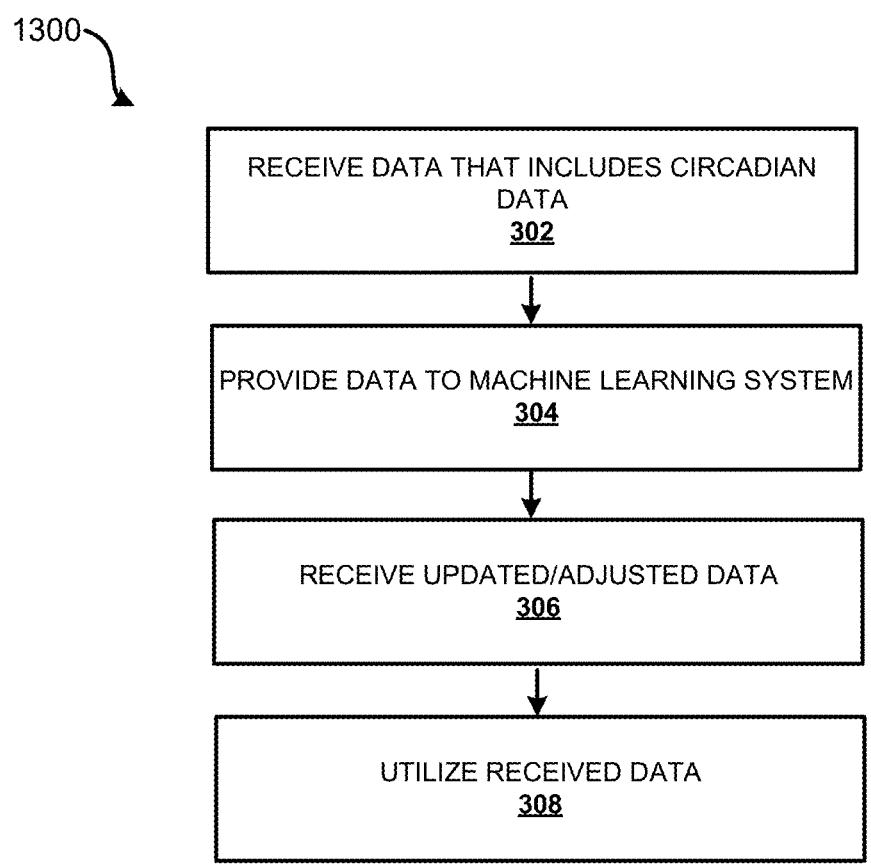
FIG. 13 is a flow diagram showing a routine illustrating aspects of a mechanism disclosed herein for utilizing data associated with circadian rhythms for improving the accuracy of at home measurements/predictions.

FIGS. 12 and 13 are flow diagrams showing routines 1200, 1300, in accordance with examples described herein. It should be appreciated that at least some of the logical operations described herein with respect to FIGS. 12 and 13, and the other FIGS., may be implemented (1) as a sequence of computer implemented acts or program modules running on a computing system and/or (2) as interconnected machine logic circuits or circuit modules within the computing system.

The implementation of the various components described herein is a matter of choice dependent on the performance and other requirements of the computing system. Accordingly, the logical operations described herein are referred to variously as operations, structural devices, acts, or modules. These operations, structural devices, acts, and modules may be implemented in software, in firmware, in special purpose digital logic and any combination thereof. It should also be appreciated that more or fewer operations may be performed than shown in the FIGS. and described herein. These operations may also be performed in parallel, or in a different order than those described herein.

FIG. 12 is a flow diagram showing routine 1200 illustrating aspects of a mechanism disclosed herein for generating predictions of clinical state/health outcomes using data obtained in a non-clinical setting.

The routine 1200 may begin at 252, where food (e.g., a meal) is selected that is consumed to evoke a nutritional response. As discussed above, the food can be a series of standardized meals, a single meal, a single food, or some other selection of food.

At 254, food data is received. An individual may log the time the food was consumed, or record the food consumed using other mechanisms. In some configurations, the timing may be based on when an image was taken of the food to consume. In other configurations, the user can be instructed to take one or more pictures of the food before, during and/or after consuming the food. A user may also provide other data relating to the food, such as but not limited to the food state (e.g., cooked/raw, an age of the food, . . . ), how long it took to consume the food, and the like. According to some examples, a computing device 102A associated with the user provides the food data 304 to a data service 120 and/or a data ingestion service.

At 256, data associated with at home tests performed to measure one or more nutritional responses are received. As discussed above, the tests are performed at one or more points in time after eating a particular food, or foods of a meal. As also discussed above, the at home tests can include blood tests, and/or other tests that measure other biomarkers. In some examples, the individual may perform a blood test. In other examples, the individual may perform some other type of test. In some examples, tests are automatically carried out by electronic data collection devices. For instance, a measure of blood glucose can be taken, or the acceleration of a smart watch recorded.

In some examples, the data ingestion service 110 can receive the data from a computing device 102 or electronic data collection device 103 associated with the individual. In other examples, the data is received from another source (e.g., the individual returns the collected biological sample via mail or some other courier service and a biological assay 109 is performed that outputs data to the data ingestion service 110). The data ingestion service 110 can also receive other data, such as circadian data.

At 258, the data can be adjusted when determined. As discussed above, the data service 120 is configured to determine whether the data is accurate. For example, was the data obtained at a proper time as indicated by the test protocol for a particular test?, was the proper data collected? (e.g., is the bloodspot filled correctly?), was the proper food consumed for the test?, was the proper amount of food consumed?, was the food properly classified?, is the sleep pattern of the user following the normal pattern for the user?, and the like. As discussed above, the data service 120 can utilize data received from the computing device 102 (e.g., timing data, image data) to assist in determining whether the test protocol was followed. The data service 120 can also utilize one or more data analysts.

At decision block 260, a decision is made as to whether to repeat the at home test and/or have the user perform a different test. As described above, the protocol may specify that the user consume two or more meals instead of one, and that the spacing of the meals be some time period. When the test is to be repeated, the process returns to 252. When the test is not to be repeated, the process flows to 262.

At 262, the data is utilized. In some examples, the data is used by a service to generate predictions of clinical state/ health outcomes. This data may have been adjusted by the data service 120. In other configurations, this data may have been provided with a weight by the data service which is taken into account by the service utilizing the data (e.g., predict one or more health outcomes for an individual), which in some cases may involve machine learning mechanisms.

FIG. 13 is a flow diagram showing routine 1300 illustrating aspects of a mechanism disclosed herein for utilizing data associated with circadian rhythms for improving the accuracy of at home measurements/predictions.

The routine 1300 may begin at 302, where data is received. As discussed above, the data can include circadian data for one or more users. The circadian data can include sleep data, HR data, temperature data, and the like.

At 304, all or a portion of the data can be provided to one or more machine learning mechanisms. As discussed above, the data can be provided to a data service 120 and/or the data can be accessed by the machine learning mechanism from a memory and/or some other data store. The machine learning mechanism can be trained to determine whether or not the circadian rhythm of a user is following a "normal" pattern or not. For instance, when the machine learning mechanism, or some other technique, determines that the user's circadian rhythm is off, the data can be adjusted. In some configurations, the machine learning mechanism is trained using thousands of samples from other users. More or fewer samples, however, can be used for training.

At 306, updated/adjusted data is received from the machine learning mechanism. As discussed above, the machine learning mechanisms can determine if the data is accurate, adjust the data (e.g., using the circadian data), adjust one or more parameters, and the like.

At 308, the data is utilized and/or stored. As discussed above, the data can be stored for later use by one or more other systems. For example, a system can utilize the adjusted data to provide one or more predictions of clinical state and/or health outcomes.

Figure 14:
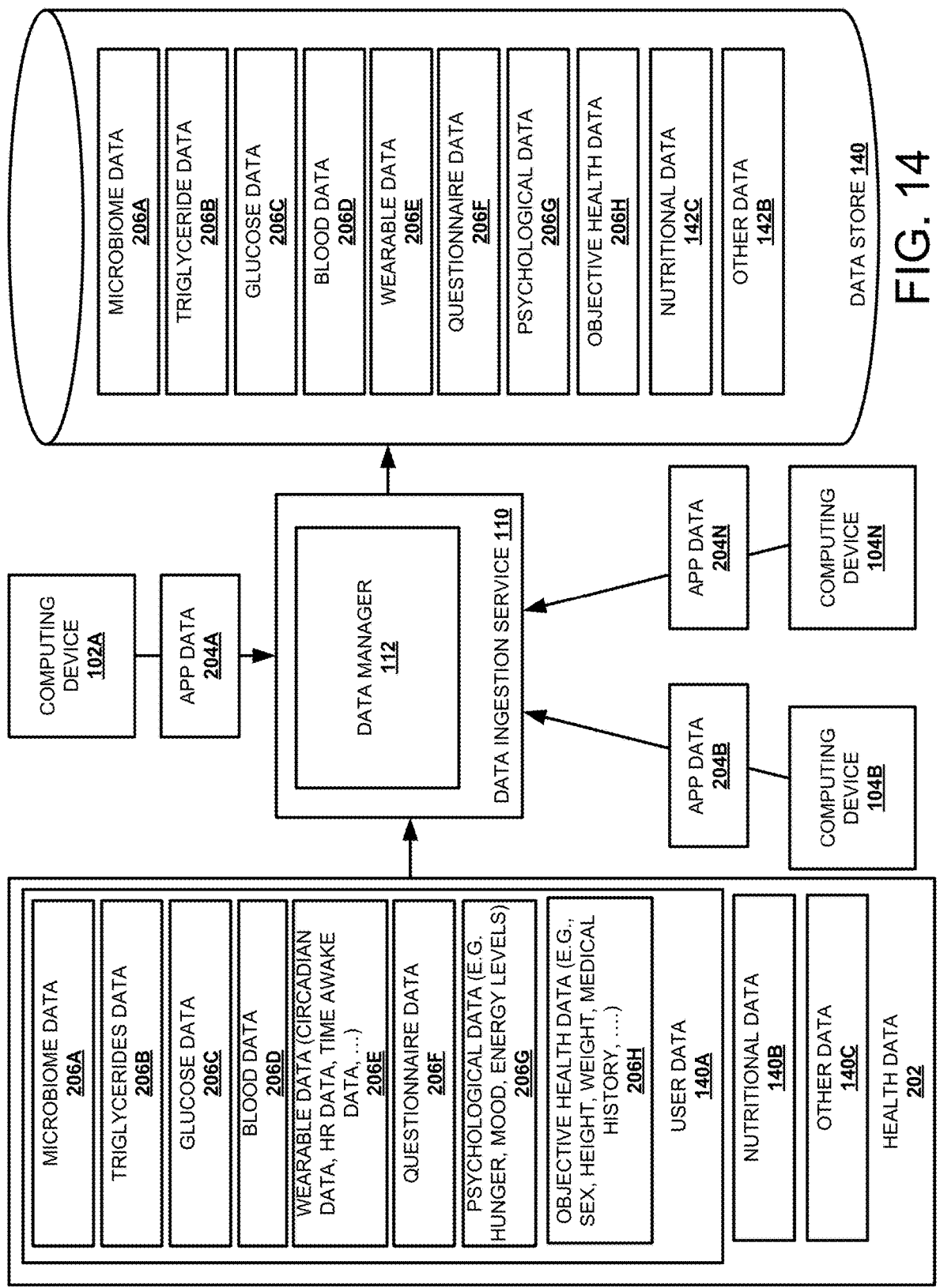
FIG. 14 is a block diagram depicting an illustrative operating environment in which a data ingestion service receives, and processes data associated with at home measurements of responses.

FIG. 14 is a block diagram depicting an illustrative operating environment 1400 in which a data ingestion service 110 receives and processes data associated with data associated with at home measurements of nutritional responses.

In some configurations, the data manager 112 is configured to receive data such as, health data 202 that can include, but is not limited to microbiome data 206A, triglycerides data 206B, glucose data 206C, blood data 206D, wearable data 206E that can include circadian data, questionnaire data 206F, psychological data (e.g., hunger, sleep quality, mood, . . . ) 206G, objective health data (e.g., height, weight, medical history, . . . ) 206H, nutritional data 140B, and other data 140C.

According to some examples, the microbiome data 206A includes data about the gut microbiome of an individual. The gut microbiome can host a large number of microbial species (e.g., >1000) that together have millions of genes.

The triglycerides data 206B may include data about triglycerides for an individual. In some examples, the triglycerides data 206B can be determined from an At Home Blood Test which in some cases is a finger prick on to a dried blood spot card. The glucose data 206C includes data about blood glucose. The glucose data 206C may be determined from various testing mechanisms, including at home measurements, such as a continuous glucose meter.

The blood data 206D may include blood tests relating to a variety of different biomarkers. As discussed above, at least some blood tests can be performed at home. In some configurations, the blood data 206D is associated with measuring blood sugar, insulin, c-peptides, triglycerides, IL-6 inflammation, ketone bodies, nutrient levels, allergy sensitivities, iron levels, blood count levels, HbA1c, and the like.

The wearable data 206E can include any data received from a computing device associated with an individual. For instance, an individual may wear an electronic data collection device 103, such as an activity-monitoring device, that monitors motion, heart rate, heart rate variability, determines how much an individual has slept that may include the types of sleep, the times an individual is awake, the number of calories burned, activities performed, blood pressure, body temperature, and the like. The individual may also wear a continuous glucose meter that monitors blood glucose levels.

The questionnaire data 206F can include data received from one or more questionnaires, and/or surveys received from one or more individuals. The psychological data 206G, that may be subjectively obtained, may include data received from the individual and/or a computing device that generates data or input based on a subjective determination (e.g., the individual states that they are still hungry after a meal, or a device estimates sleep quality based on the movement of the user at night perhaps combined with heart rate data). The objective health data 206H includes data that can be objectively measured, such as but not limited to height, weight, medical history, and the like.

The nutritional data 140B can include data about food, which is referred to herein as "food data". For example, the nutritional data can include nutritional information about different food(s) such as their macronutrients and micronutrients or the bioavailability of its nutrients under different conditions (raw vs cooked, or whole vs ground up).

The other data 142B can include other data associated with the individual. For example, the other data 142B can include data that can be received directly from a computer application that logs information for an individual (e.g., food eaten, sleep, . . . ) and/or from the user via a user interface.

In some examples, different computing devices 102 associated with different users provide application data 204 to the data manager 112 for ingestion by the data ingestion service 110. As illustrated, computing device 102A provides app data 204A to the data manager 112, computing device 104B provides app data 204B to the data manager 112, and computing device 104N provides app data 204N to the data manager 112. There may be any number of computing devices utilized.

As discussed briefly above, the data manager 112 receives data from different data sources, processes the data when needed (e.g., cleans up the data for storage in a uniform manner), and stores the data within one or more data stores, such as the data store 140.

The data manager 112 can be configured to perform processing on the data before storing the data in the data store 140. For example, the data manager 112 may receive data for ketone bodies and then use that data to generate ketone body ratios. Similarly, the data manager 112 may process food eaten and generate meal calories, number of carbohydrates, fat to carbohydrate rations, how much fiber consumed during a time period, and the like. The data stored in the data store 140, or some other location, can be utilized by the data service 120 to determine an accuracy of at home measurements of nutritional responses performed by users. The data outputted by the data service 108B to the nutritional service may therefore contain different values than are stored in the data store 140, for example if a food quantity is adjusted.

Figure 15:
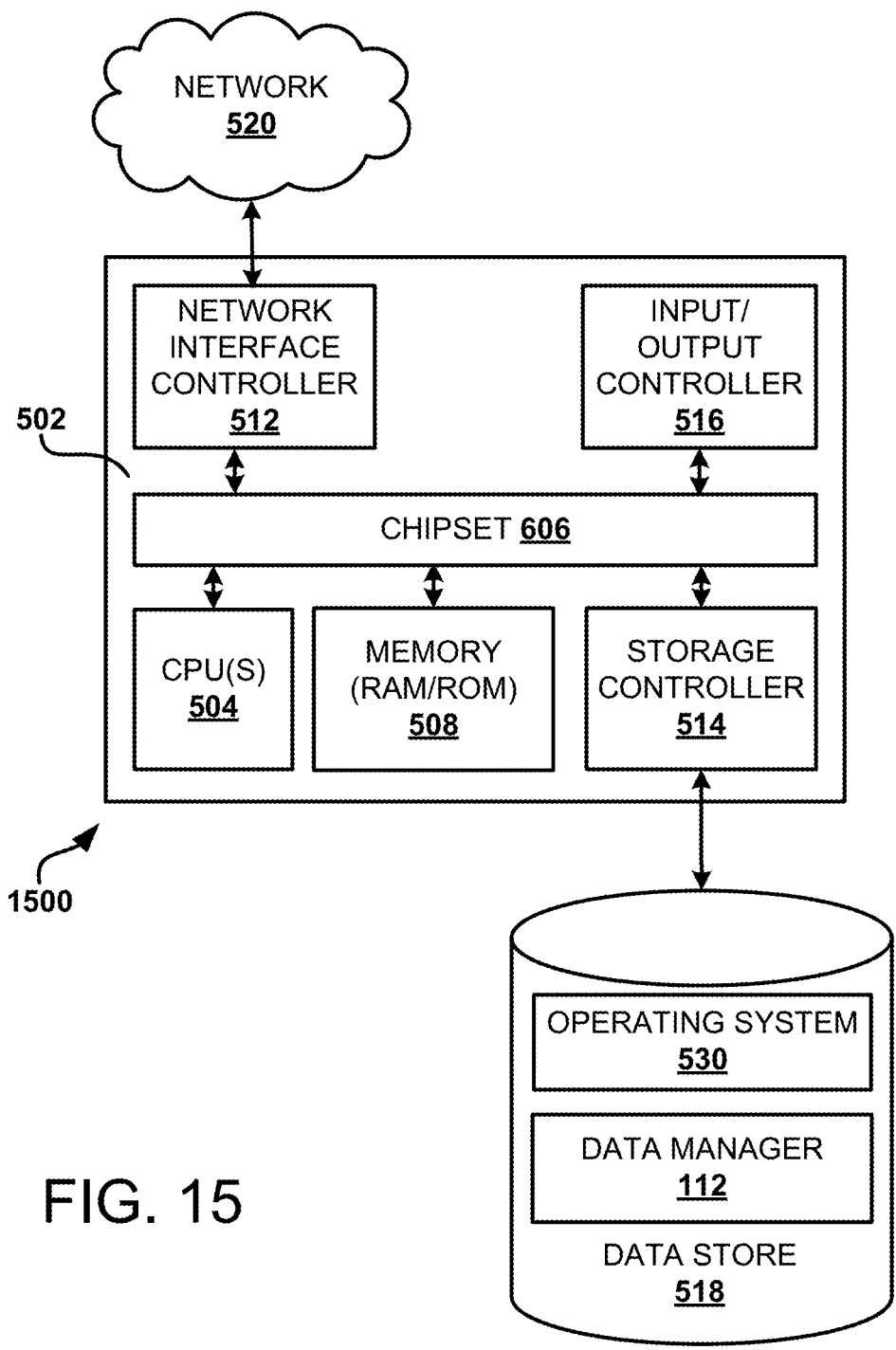
FIG. 15 is a computer architecture diagram showing one illustrative computer hardware architecture for implementing a computing device that might be utilized to implement aspects of the various examples presented herein.

FIG. 15 shows an example computer architecture for a computer 1500. The computer architecture shown in FIG. 15 illustrates a conventional server computer, workstation, desktop computer, laptop, mobile device, tablet, network appliance, digital cellular phone, smart watch, or other computing device, and may be utilized to execute any of the software components presented herein. For example, the computer architecture shown in FIG. 15 may be utilized to execute software components for performing operations as described above. The computer architecture shown in FIG. 15 might also be utilized to implement a computing device 102, or any other of the computing systems described herein.

The computer 1500 includes a baseboard 502, or "motherboard," to which a multitude of components or devices may be connected by way of a system bus or other electrical communication paths. In one illustrative example, one or more central processing units ("CPUs") 504 operate in conjunction with a chipset 506. The CPUs 504 may be standard programmable processors that perform arithmetic and logical operations necessary for the operation of the computer 1500.

The chipset 506 provides an interface between the CPUs 504 and the remainder of the components and devices on the baseboard 502. The chipset 506 may provide an interface to memory 506, such as RAM and/or read-only memory ("ROM"). The memory may store software components utilized for the operation of the computer 1500 in accordance with the examples described herein.

The computer 1500 may operate in a networked environment using logical connections to remote computing devices and computer systems through a network, such as the network 520. The chipset 506 may include functionality for providing network connectivity through a network interface controller, such as a cellular network adapter, WiFi network adapter, Ethernet adapter, and the like. The NIC 512 is capable of connecting the computer 1500 to other computing devices over the network 520.

The computer 1500 may be connected to a mass storage device 516 that provides storage for the computer. The mass storage device 516 may store system programs, application programs, other program modules and data, which have been described in greater detail herein. The mass storage device 516 may be connected to the computer 1500 through a storage controller 514 connected to the chipset 506. The mass storage device 516 may consist of one or more physical storage units. The storage controller 514 may interface with the physical storage units through various type of interfaces.

The mass storage device 516 described above, the computer 1500 may have access to other computer-readable storage media to store and retrieve information, such as program modules, data structures, or other data. By way of example, and not limitation, computer-readable storage media may include volatile and non-volatile, removable and non-removable media implemented in any method or technology.

The mass storage device 516 may store an operating system 530 utilized to control the operation of the computer 1500. According to some configurations, the operating system may include, but is not limited to the UNIX operating system, the LINUX operating system, the WINDOWS® operating system from MICROSOFT Corporation, the iOS operating system from APPLE Corporation, the ANDROID operating system from GOOGLE, and the like. Other operating systems may also be utilized. The mass storage device 516 may store other system or application programs and data utilized by the computer 1500, such as components that include the data manager 122, and/or any of the other software components and data described above. The mass storage device 516 might also store other programs and data not specifically identified herein.

In one example, the mass storage device 516 or other computer-readable storage media is encoded with computer-executable instructions that, when loaded into the computer 1500, implement the examples described herein. The computer 1500 has access to computer-readable storage media storing computer-executable instructions which, when executed by the computer 1500, may be configured to perform the various routines described above. The computer 1500 might also include computer-readable storage media for performing any of the other computer-implemented operations described herein.

The computer 1500 may also include one or more input/output controllers 516 for receiving and processing input from a number of input devices, such as an electronic data collection device, a keyboard, a mouse, a touchpad, a touch screen, an electronic stylus, or other type of input device. Similarly, the input/output controller 516 may provide output to one or more types of output devices (e.g., a display, a projector, a printer, . . . ). The computer 1500 may not include all of the components shown in FIG. 15, may include other components that are not explicitly shown in FIG. 15, or may utilize an architecture completely different than that shown in FIG. 15.

Based on the foregoing, it should be appreciated that technologies for using at home measurements to predict clinical state and health outcomes and improve the accuracy of the at home measurements/predications using various data have been presented herein. Moreover, although some of the subject matter presented herein has been described in language specific to computer structural features, methodological acts and computer readable media, it is to be understood that the invention defined in the appended claims is not necessarily limited to the specific features, acts, or media described herein. Rather, the specific features, acts and media are disclosed as example forms of implementing at least some of the claims.

The subject matter described above is provided by way of illustration only and should not be construed as limiting. Furthermore, the claimed subject matter is not limited to implementations that solve any or all disadvantages noted in any part of this disclosure. Various modifications and changes may be made to the subject matter described herein without following the examples and applications illustrated and described, and without departing from the true spirit and scope of the present invention, which is set forth in the following claims.

What is claimed is:

1. A method, comprising:
creating a training data set from data that is associated with a plurality of users, wherein the data is accessed from a data store and includes one or more of first data associated with performance of one or more first tests, second data associated with performance of one or more second tests, and target prediction data of at least one of one or more values of a biomarker, a clinical state, a disease risk, or a health outcome;
training, via one or more computers, a machine learning mechanism using the training data set, wherein the machine learning mechanism is to be used to make improved predictions of at least one of one or more clinical states, one or more disease risks, one or more biomarkers, and one or more health outcomes;
receiving, via the one or more computers or one or more second computers, first data associated with performance of one or more first tests, performed at a first time in a non-clinical setting, that are associated with an identification of one or more nutritional responses evoked in response to a combination of a first meal consumed by a user and a second meal consumed by the user, wherein the second meal is consumed within a specified time of the first meal on a same day;
receiving, via the one or more computers or the one or more second computers, second data associated with performance of one or more second tests performed at a second time in the non-clinical setting, wherein the second time is a specified time from the first time;
aggregating the first data and the second data with aggregated data obtained from other users;
causing the machine learning mechanism, trained using the training data set, to execute on the one or more computers or the one or more second computers, wherein executing the machine learning mechanism includes performing actions, to
generate, using the machine learning mechanism, that uses at least a portion of the aggregated data, prediction data that includes one or more predictions for the user of at least one of one or more values of a biomarker, a clinical state, a disease risk, or a health outcome;
generating a user interface that when displayed includes the prediction data for the user; and
causing the user interface, that includes the prediction data, to be displayed on a computing device associated with the user.

2. The method of claim 1, further comprising
determining an accuracy of the first data and the second data; and
confirming that the first data and the second data are accurate, and wherein the one or more first tests are associated with two or more of insulin, glucose, c-peptide, ketone bodies, triglycerides, IL-6, inflammation, or microbiome.

3. The method of claim 1, wherein the performance of at least one of the one or more first tests or the one or more seconds tests includes collecting first blood for the user in the non-clinical setting at the first time to measure a post-prandial response, and collecting second blood for the user in the non-clinical setting at the second time to measure the postprandial response, and generating, based on the first blood and the second blood, readings for different biomarkers that include a measurement of triglycerides, and predicting a level of remnant lipoproteins.

4. The method of claim 1, wherein the first meal is consumed after a fasting state of the user, and wherein performance of the one or more first tests or the one or more second tests includes collecting blood, in the non-clinical setting, and generating, based at least in part on the blood and second blood collected from the user during the fasting state, a measurement of c-peptide, and predicting, via the one or more computers, one or more insulin levels from a value of c-peptide.

5. The method of claim 1, wherein the one or more first tests and the one or more second tests include measuring lipid responses and glucose responses.

6. The method of claim 1, further comprising:
causing a first reminder to be provided to a computing device associated with the user, wherein the first reminder instructs the user to consume the second meal at the specified time from the first meal;
causing a second reminder to be provided to the computing device associated with the user, wherein the second reminder instructs the user obtain at least one of blood or one or more measurements after the first reminder; and
causing a third reminder to be provided to the computing device associated with the user, wherein the third reminder instructs the user obtain at least one of blood or one or more measurements after the second reminder.

7. The method of claim 1, further comprising:
predicting a time of a peak for a biomarker for a user; and
providing an indication to the computing device of the user to obtain at least one of blood or a measurement within a specified time of the time of the peak for the biomarker.

8. The method of claim 1, further comprising:
receiving from a computing device associated with the user, circadian data that is obtained in a non-clinical setting, wherein the circadian data includes sleep data, and heart rate data;
providing the circadian data to the machine learning mechanism that uses the circadian data to programmatically adjust the prediction data; and
generating one or more nutritional recommendations for the user, wherein the one or more nutritional recommendations indicate a first effect that a time at which the user eats a meal has on a response to the meal, and a second effect of a change to a circadian rhythm.

9. The method of claim 1, further comprising predicting one or more post-prandial measures of the user based at least in part on an abundance of microbiome species of the user.

10. A system, comprising:
one or more processors, configured to perform actions including:
creating a training data set from data that is associated with a plurality of users, wherein the data is accessed from a data store and includes one or more of first data associated with performance of one or more first tests, second data associated with performance of one or more second tests, and target prediction data of at least one of one or more values of a biomarker, a clinical state, a disease risk, or a health outcome;
training a machine learning mechanism using the training data set, wherein the machine learning mechanism is to be used to make improved predictions of at least one of one or more clinical states, one or more disease risks, one or more biomarkers, and one or more health outcomes;

accessing, via the one or more processors or one or more second processors, first data associated with performance of one or more first tests, performed at a first time in a non-clinical setting, that are associated with an identification of one or more nutritional responses evoked in response to a combination of a first meal consumed by a user and a second meal consumed by the user, wherein the second meal is consumed within a specified time of the first meal on a same day;

accessing, via the one or more processors or the one or more second processors, second data associated with performance of one or more second tests performed at a second time in the non-clinical setting, wherein the second time is a specified time from the first time;

aggregating the first data and the second data with aggregated data obtained from other users;

causing the machine learning mechanism, trained using the training data set, to execute on the one or more processors or the one or more second processors, wherein executing the machine learning mechanism includes performing actions, to generate, using the machine learning mechanism that uses at least a portion of the aggregated data, prediction data that includes one or more predictions for the user of at least one of one or more values of a biomarker, a clinical state, a disease risk, or a health outcome;

generating a user interface that when displayed includes at least a portion of the prediction data that is associated with the one or more predictions for the user; and causing the user interface, that includes at least the portion of the prediction data, to be displayed on a computing device associated with the user.

11. The system of claim 10, wherein the actions further include:

determining that at least one of the first data and the second data are inaccurate; and programmatically adjusting the at least one of the fist data and the second data that are inaccurate, and wherein the first data and the second data are associated with two or more of insulin, glucose, c-peptide, ketone bodies, triglycerides, IL-6, inflammation, or microbiome.

12. The system of claim 10, wherein the performance of at least one of the one or more first tests or the one or more second tests includes collecting first blood for the user in the non-clinical setting at the first time to measure a postprandial response, and collecting second blood for the user in the non-clinical setting at the second time to measure the postprandial response, and generating, based on the first blood and the second blood, readings for different biomarkers that include a measurement of triglycerides, and predicting a level of remnant lipoproteins.

13. The system of claim 10, the actions further comprising:

causing a first reminder to be provided to a computing device associated with the user, wherein the first reminder instructs the user to consume the second meal at the specified time from the first meal;

predicting a time of a peak for a biomarker for the user; and causing one or more second reminders to be provided to the computing device associated with the user, wherein the one or more second reminders instructs the user obtain at least one of blood or measurements after the second meal at different times.

14. The system of claim 10, further comprising:

receiving from a computing device associated with the user, circadian data that is obtained in a non-clinical setting, wherein the circadian data includes sleep data, and heart rate data;

providing the circadian data to the machine learning mechanism that uses the circadian data to programmatically adjust the prediction data; and generating one or more nutritional recommendations for the user, wherein the one or more nutritional recommendations indicate a first effect that a time at which the user eats a meal has on a response to the meal, and a second effect of a change to a circadian rhythm.

15. The system of claim 10, further comprising predicting one or more post-prandial measures of the user based at least in part on an abundance of microbiome species of the user.

16. A non-transitory computer-readable storage medium having computer-executable instructions stored thereupon which, when executed by a computer, cause the computer to perform actions comprising:

creating a training data set from data that is associated with a plurality of users, wherein the data is accessed from a data store and includes one or more of first data associated with performance of one or more first tests, second data associated with performance of one or more second tests, and target prediction data of at least one of one or more values of a biomarker, a clinical state, a disease risk, or a health outcome;

training a machine learning mechanism using the training data set, wherein the machine learning mechanism is to be used to make improved predictions of at least one of one or more clinical states, one or more disease risks, one or more biomarkers, and one or more health outcomes;

accessing first data associated with performance of one or more first tests, performed at a first time in a non-clinical setting, that are associated with an identification of one or more nutritional responses evoked in response to a combination of a first meal consumed by a user and a second meal consumed by the user, wherein the second meal is consumed within a specified time of the first meal on a same day;

accessing second data associated with performance of one or more second tests performed at a second time in the non-clinical setting, wherein the second time is a specified time from the first time;

aggregating the first data and the second data with aggregated data obtained from other users;

causing the machine learning mechanism, trained using the training data set, to execute on the computer or one or more other computers, wherein executing the machine learning mechanism includes performing actions, to generate, using the machine learning mechanism that uses at least a portion of the aggregated data, prediction data that includes one or more predictions for the user of at least one of one or more values of a biomarker, a clinical state, a disease risk, or a health outcome;

generating a user interface that when displayed includes at least a portion of the prediction data that is associated with the one or more predictions for the user; and causing the user interface, that includes at least the portion of the prediction data, to be displayed on a computing device associated with the user.

17. The non-transitory computer-readable storage medium of claim 16, wherein the actions further include:

determining that one or more of the first data and the second data are inaccurate; and programmatically adjusting the one or more of the fist data and the second data that are inaccurate, and wherein the first data and the second data are associated with two or more of insulin, glucose, c-peptide, ketone bodies, triglycerides, IL-6, inflammation, or microbiome.

18. The non-transitory computer-readable storage medium of claim 16, wherein the performance of at least one of the one or more first tests or the one or more second tests includes collecting first blood for the user in the non-clinical setting at the first time to measure a postprandial response, and collecting second blood for the user in the non-clinical setting at the second time to measure the postprandial response, and generating, based on the first blood and the second blood, readings for different biomarkers that include a measurement of triglycerides, and predicting a level of remnant lipoproteins.

19. The non-transitory computer-readable storage medium of claim 16, further comprising:

receiving from a computing device associated with the user, circadian data that is obtained in a non-clinical setting, wherein the circadian data includes sleep data, and heart rate data;

providing the circadian data to the machine learning mechanism that uses the circadian data to programmatically adjust the prediction data; and generating one or more nutritional recommendations for the user, wherein the one or more nutritional recommendations indicate a first effect that a time at which the user eats a meal has on a response to the meal, and a second effect of a change to a circadian rhythm.

20. The non-transitory computer-readable storage medium of claim 16, further comprising predicting one or more post-prandial measures of the user based at least in part on an abundance of microbiome species of the user.

* * * * *